United States Patent
Misener et al.

(10) Patent No.: US 12,137,989 B2
(45) Date of Patent: Nov. 12, 2024

(54) SYSTEMS AND METHODS FOR INTELLIGENT ULTRASOUND PROBE GUIDANCE

(71) Applicant: Bard Access Systems, Inc., Salt Lake City, UT (US)

(72) Inventors: Anthony K. Misener, Bountiful, UT (US); Steffan Sowards, Salt Lake City, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 17/861,031

(22) Filed: Jul. 8, 2022

(65) Prior Publication Data

US 2024/0008929 A1    Jan. 11, 2024

(51) Int. Cl.
*A61B 8/14*    (2006.01)
*A61B 8/00*    (2006.01)
(Continued)

(52) U.S. Cl.
CPC ............ *A61B 34/20* (2016.02); *A61B 8/0841* (2013.01); *A61B 8/085* (2013.01); *A61B 8/4254* (2013.01);
(Continued)

(58) Field of Classification Search
CPC ....... A61B 34/20; A61B 8/0841; A61B 8/085; A61B 8/4254; A61B 8/4488;
(Continued)

(56) References Cited

U.S. PATENT DOCUMENTS 5,148,809 A    9/1992    Biegeleisen-Knight et al.
5,181,513 A    1/1993    Touboul et al.
(Continued)

FOREIGN PATENT DOCUMENTS

AU    2006201646 A1    11/2006
CN    114129137 B  *  9/2022
(Continued)

OTHER PUBLICATIONS

Stolka, P.J., et al., (2014). Needle Guidance Using Handheld Stereo Vision and Projection for Ultrasound-Based Interventions. In: Galland, P., Hata, N., Barillot, C., Hornegger, J., Howe, R. (eds) Medical Image Computing and Computer-Assisted Intervention—MICCAI 2014. MICCAI 2014. (Year: 2014).
(Continued)

*Primary Examiner* — Mark D Remaly
(74) *Attorney, Agent, or Firm* — Rutan & Tucker LLP

(57) ABSTRACT

Disclosed is an ultrasound probe including an array of ultrasonic transducers and an orientation system, wherein the orientation system obtains orientation information of the ultrasound probe. Also disclosed is a console for communicating with the ultrasound probe, the console including one or more processors and non-transitory computer-readable medium having stored thereon logic, when executed by the one or more processors, causes operations including: obtaining the orientation information, performing an identification process on the ultrasound signals to identify an anatomical target (target vessel), determining, based on the orientation information, a direction of movement required by the ultrasound probe to place the ultrasound probe at a position relative to the ultrasound probe over the anatomical target, and initiating provision of feedback of the ultrasound probe indicating the direction of movement required by the
(Continued)

ultrasound probe to place the ultrasound probe at a position relative to the ultrasound probe over the anatomical target.

17 Claims, 14 Drawing Sheets

(51) Int. Cl.
    *A61B 8/08*                 (2006.01)
    *A61B 34/20*             (2016.01)

(52) U.S. Cl.
    CPC .... *A61B 8/4488* (2013.01); *A61B 2034/2055* (2016.02); *A61B 2034/2063* (2016.02)

(58) Field of Classification Search
    CPC .... A61B 2034/2055; A61B 2034/2063; A61B 2562/0233; A61B 5/065; A61B 8/467
    See application file for complete search history.

(56) References Cited

U.S. PATENT DOCUMENTS

| | | |
|---|---|---|
| 5,325,293 A | 6/1994 | Dorne |
| 5,441,052 A | 8/1995 | Miyajima |
| 5,549,554 A | 8/1996 | Miraki |
| 5,573,529 A | 11/1996 | Haak et al. |
| 5,775,322 A | 7/1998 | Silverstein et al. |
| 5,879,297 A | 3/1999 | Haynor et al. |
| 5,908,387 A | 6/1999 | LeFree et al. |
| 5,967,984 A | 10/1999 | Chu et al. |
| 5,970,119 A | 10/1999 | Hofmann |
| 6,004,270 A | 12/1999 | Urbano et al. |
| 6,019,724 A | 2/2000 | Gronningsaeter et al. |
| 6,068,599 A | 5/2000 | Saito et al. |
| 6,074,367 A | 6/2000 | Hubbell |
| 6,129,668 A | 10/2000 | Haynor et al. |
| 6,132,379 A | 10/2000 | Patacsil et al. |
| 6,216,028 B1 | 4/2001 | Haynor et al. |
| 6,233,476 B1 | 5/2001 | Strommer et al. |
| 6,245,018 B1 | 6/2001 | Lee |
| 6,263,230 B1 | 7/2001 | Haynor et al. |
| 6,375,615 B1 | 4/2002 | Flaherty et al. |
| 6,436,043 B2 | 8/2002 | Bonnefous |
| 6,498,942 B1 | 12/2002 | Esenaliev et al. |
| 6,503,205 B2 | 1/2003 | Manor et al. |
| 6,508,769 B2 | 1/2003 | Bonnefous |
| 6,511,458 B2 | 1/2003 | Milo et al. |
| 6,524,249 B2 | 2/2003 | Moehring et al. |
| 6,543,642 B1 | 4/2003 | Milliorn |
| 6,554,771 B1 | 4/2003 | Buil et al. |
| 6,592,520 B1 | 7/2003 | Peszynski et al. |
| 6,592,565 B2 | 7/2003 | Twardowski |
| 6,601,705 B2 | 8/2003 | Molina et al. |
| 6,612,992 B1 | 9/2003 | Hossack et al. |
| 6,613,002 B1 | 9/2003 | Clark et al. |
| 6,623,431 B1 | 9/2003 | Sakuma et al. |
| 6,641,538 B2 | 11/2003 | Nakaya et al. |
| 6,647,135 B2 | 11/2003 | Bonnefous |
| 6,687,386 B1 | 2/2004 | Ito et al. |
| 6,749,569 B1 | 6/2004 | Pellegretti |
| 6,754,608 B2 | 6/2004 | Svanerudh et al. |
| 6,755,789 B2 | 6/2004 | Stringer et al. |
| 6,840,379 B2 | 1/2005 | Franks-Farah et al. |
| 6,857,196 B2 | 2/2005 | Dalrymple |
| 6,979,294 B1 | 12/2005 | Selzer et al. |
| 7,074,187 B2 | 7/2006 | Selzer et al. |
| 7,244,234 B2 | 7/2007 | Ridley et al. |
| 7,359,554 B2 | 4/2008 | Klingensmith et al. |
| 7,534,209 B2 | 5/2009 | Abend et al. |
| 7,599,730 B2 | 10/2009 | Hunter et al. |
| 7,637,870 B2 | 12/2009 | Flaherty et al. |
| 7,681,579 B2 | 3/2010 | Schwartz |
| 7,691,061 B2 | 4/2010 | Hirota |
| 7,699,779 B2 | 4/2010 | Sasaki et al. |
| 7,720,520 B2 | 5/2010 | Willis |
| 7,727,153 B2 | 6/2010 | Fritz et al. |
| 7,734,326 B2 | 6/2010 | Pedain et al. |
| 7,831,449 B2 | 11/2010 | Ying et al. |
| 7,905,837 B2 | 3/2011 | Suzuki |
| 7,925,327 B2 | 4/2011 | Weese |
| 7,927,278 B2 | 4/2011 | Selzer et al. |
| 8,014,848 B2 | 9/2011 | Birkenbach et al. |
| 8,050,523 B2 | 11/2011 | Younge et al. |
| 8,060,181 B2 | 11/2011 | Rodriguez Ponce et al. |
| 8,068,581 B2 | 11/2011 | Boese et al. |
| 8,075,488 B2 | 12/2011 | Burton |
| 8,090,427 B2 | 1/2012 | Eck et al. |
| 8,105,239 B2 | 1/2012 | Specht |
| 8,172,754 B2 | 5/2012 | Watanabe et al. |
| 8,175,368 B2 | 5/2012 | Sathyanarayana |
| 8,200,313 B1 | 6/2012 | Rambod et al. |
| 8,211,023 B2 | 7/2012 | Swan et al. |
| 8,228,347 B2 | 7/2012 | Beasley et al. |
| 8,298,147 B2 | 10/2012 | Huennekens et al. |
| 8,303,505 B2 | 11/2012 | Webler et al. |
| 8,323,202 B2 | 12/2012 | Roschak et al. |
| 8,328,727 B2 | 12/2012 | Miele et al. |
| 8,388,541 B2 | 3/2013 | Messerly et al. |
| 8,409,103 B2 | 4/2013 | Grunwald et al. |
| 8,449,465 B2 | 5/2013 | Nair et al. |
| 8,553,954 B2 | 10/2013 | Saikia |
| 8,556,815 B2 | 10/2013 | Pelissier et al. |
| 8,585,600 B2 | 11/2013 | Liu et al. |
| 8,622,913 B2 | 1/2014 | Dentinger et al. |
| 8,706,457 B2 | 4/2014 | Hart et al. |
| 8,727,988 B2 | 5/2014 | Flaherty et al. |
| 8,734,357 B2 | 5/2014 | Taylor |
| 8,744,211 B2 | 6/2014 | Owen |
| 8,754,865 B2 | 6/2014 | Merritt et al. |
| 8,764,663 B2 | 7/2014 | Smok et al. |
| 8,781,194 B2 | 7/2014 | Malek et al. |
| 8,781,555 B2 | 7/2014 | Burnside et al. |
| 8,790,263 B2 | 7/2014 | Randall et al. |
| 8,849,382 B2 | 9/2014 | Cox et al. |
| 8,939,908 B2 | 1/2015 | Suzuki et al. |
| 8,961,420 B2 | 2/2015 | Zhang |
| 9,022,940 B2 | 5/2015 | Meier |
| 9,138,290 B2 | 9/2015 | Hadjicostis |
| 9,155,517 B2 | 10/2015 | Dunbar et al. |
| 9,204,858 B2 | 12/2015 | Pelissier et al. |
| 9,220,477 B2 | 12/2015 | Urabe et al. |
| 9,257,220 B2 | 2/2016 | Nicholls et al. |
| 9,295,447 B2 | 3/2016 | Shah |
| 9,320,493 B2 | 4/2016 | Visveshwara |
| 9,357,980 B2 | 6/2016 | Toji et al. |
| 9,364,171 B2 | 6/2016 | Harris et al. |
| 9,427,207 B2 | 8/2016 | Sheldon et al. |
| 9,445,780 B2 | 9/2016 | Hossack et al. |
| 9,456,766 B2 | 10/2016 | Cox et al. |
| 9,456,804 B2 | 10/2016 | Tamada |
| 9,459,087 B2 | 10/2016 | Dunbar et al. |
| 9,468,413 B2 | 10/2016 | Hall et al. |
| 9,492,097 B2 | 11/2016 | Wilkes et al. |
| 9,521,961 B2 | 12/2016 | Silverstein et al. |
| 9,554,716 B2 | 1/2017 | Burnside et al. |
| 9,582,876 B2 | 2/2017 | Specht |
| 9,597,008 B2 | 3/2017 | Henkel et al. |
| 9,610,061 B2 | 4/2017 | Ebbini et al. |
| 9,636,031 B2 | 5/2017 | Cox |
| 9,649,037 B2 | 5/2017 | Lowe et al. |
| 9,649,048 B2 | 5/2017 | Cox et al. |
| 9,702,969 B2 | 7/2017 | Hope Simpson et al. |
| 9,715,757 B2 | 7/2017 | Ng et al. |
| 9,717,415 B2 | 8/2017 | Cohen et al. |
| 9,731,066 B2 | 8/2017 | Liu et al. |
| 9,814,433 B2 | 11/2017 | Benishti et al. |
| 9,814,531 B2 | 11/2017 | Yagi et al. |
| 9,861,337 B2 | 1/2018 | Patwardhan et al. |
| 9,895,138 B2 | 2/2018 | Sasaki |
| 9,913,605 B2 | 3/2018 | Harris et al. |
| 9,949,720 B2 | 4/2018 | Southard et al. |
| 10,043,272 B2 | 8/2018 | Forzoni et al. |
| 10,380,919 B2 | 8/2019 | Savitsky et al. |
| 10,380,920 B2 | 8/2019 | Savitsky et al. |

(56) References Cited

U.S. PATENT DOCUMENTS

| | | |
|---|---|---|
| 10,424,225 B2 | 9/2019 | Nataneli et al. |
| 10,434,278 B2 | 10/2019 | Dunbar et al. |
| 10,449,330 B2 | 10/2019 | Newman et al. |
| 10,524,691 B2 | 1/2020 | Newman et al. |
| 10,674,935 B2 | 6/2020 | Henkel et al. |
| 10,751,509 B2 | 8/2020 | Misener |
| 10,758,155 B2 | 9/2020 | Henkel et al. |
| 10,765,343 B2 | 9/2020 | Henkel et al. |
| 10,896,628 B2 | 1/2021 | Savitsky et al. |
| 11,062,624 B2 | 7/2021 | Savitsky et al. |
| 11,120,709 B2 | 9/2021 | Savitsky et al. |
| 11,311,269 B2 | 4/2022 | Dunbar et al. |
| 11,315,439 B2 | 4/2022 | Savitsky et al. |
| 11,600,201 B1 | 3/2023 | Savitsky et al. |
| 2002/0038088 A1 | 3/2002 | Imran et al. |
| 2002/0148277 A1 | 10/2002 | Umeda |
| 2003/0047126 A1 | 3/2003 | Tomaschko |
| 2003/0060714 A1 | 3/2003 | Henderson et al. |
| 2003/0073900 A1 | 4/2003 | Senarith et al. |
| 2003/0093001 A1 | 5/2003 | Martikainen |
| 2003/0106825 A1 | 6/2003 | Molina et al. |
| 2003/0120154 A1 | 6/2003 | Sauer et al. |
| 2004/0055925 A1 | 3/2004 | Franks-Farah et al. |
| 2005/0000975 A1 | 1/2005 | Carco et al. |
| 2005/0049504 A1 | 3/2005 | Lo et al. |
| 2005/0165299 A1 | 7/2005 | Kressy et al. |
| 2005/0251030 A1 | 11/2005 | Azar et al. |
| 2005/0267365 A1 | 12/2005 | Sokulin et al. |
| 2006/0013523 A1 | 1/2006 | Childers et al. |
| 2006/0015039 A1 | 1/2006 | Cassidy et al. |
| 2006/0020204 A1 | 1/2006 | Serra et al. |
| 2006/0079781 A1 | 4/2006 | Germond-Rouet et al. |
| 2006/0184029 A1 | 8/2006 | Haim et al. |
| 2006/0210130 A1 | 9/2006 | Germond-Rouet et al. |
| 2007/0043341 A1 | 2/2007 | Anderson et al. |
| 2007/0049822 A1 | 3/2007 | Bunce et al. |
| 2007/0073155 A1 | 3/2007 | Park et al. |
| 2007/0199848 A1 | 8/2007 | Ellswood et al. |
| 2007/0239120 A1 | 10/2007 | Brock et al. |
| 2007/0249911 A1 | 10/2007 | Simon |
| 2008/0021322 A1 | 1/2008 | Stone et al. |
| 2008/0033293 A1 | 2/2008 | Beasley et al. |
| 2008/0033759 A1 | 2/2008 | Finlay |
| 2008/0051657 A1 | 2/2008 | Rold |
| 2008/0146915 A1 | 6/2008 | McMorrow |
| 2008/0177186 A1 | 7/2008 | Slater et al. |
| 2008/0221425 A1 | 9/2008 | Olson et al. |
| 2008/0294037 A1 | 11/2008 | Richter |
| 2008/0300491 A1 | 12/2008 | Bonde et al. |
| 2009/0012399 A1 | 1/2009 | Sunagawa et al. |
| 2009/0143672 A1 | 6/2009 | Harms et al. |
| 2009/0143684 A1 | 6/2009 | Cermak et al. |
| 2009/0156926 A1 | 6/2009 | Messerly et al. |
| 2009/0306509 A1 | 12/2009 | Pedersen et al. |
| 2010/0020926 A1 | 1/2010 | Boese et al. |
| 2010/0106015 A1 | 4/2010 | Norris |
| 2010/0179428 A1 | 7/2010 | Pedersen et al. |
| 2010/0211026 A2 | 8/2010 | Sheetz et al. |
| 2010/0277305 A1 | 11/2010 | Garner et al. |
| 2010/0286515 A1 | 11/2010 | Gravenstein et al. |
| 2010/0312121 A1 | 12/2010 | Guan |
| 2011/0002518 A1 | 1/2011 | Ziv-Ari et al. |
| 2011/0071404 A1 | 3/2011 | Schmitt et al. |
| 2011/0295108 A1 | 12/2011 | Cox et al. |
| 2011/0313293 A1 | 12/2011 | Lindekugel et al. |
| 2012/0179038 A1 | 7/2012 | Meurer et al. |
| 2012/0197132 A1 | 8/2012 | O'Connor |
| 2012/0209121 A1 | 8/2012 | Boudier |
| 2012/0220865 A1 | 8/2012 | Brown et al. |
| 2012/0238875 A1 | 9/2012 | Savitsky et al. |
| 2012/0277576 A1 | 11/2012 | Lui |
| 2013/0041250 A1 | 2/2013 | Pelissier et al. |
| 2013/0102889 A1 | 4/2013 | Southard et al. |
| 2013/0131499 A1* | 5/2013 | Chan ............... A61B 8/0841 |
| | | 600/424 |
| 2013/0131502 A1 | 5/2013 | Blaivas et al. |
| 2013/0150724 A1 | 6/2013 | Blaivas et al. |
| 2013/0188832 A1 | 7/2013 | Ma et al. |
| 2013/0218024 A1 | 8/2013 | Boctor et al. |
| 2013/0324840 A1 | 12/2013 | Zhongping et al. |
| 2014/0005530 A1 | 1/2014 | Liu et al. |
| 2014/0031690 A1 | 1/2014 | Toji et al. |
| 2014/0036091 A1 | 2/2014 | Zalev et al. |
| 2014/0073976 A1 | 3/2014 | Fonte et al. |
| 2014/0100440 A1 | 4/2014 | Cheline et al. |
| 2014/0155737 A1 | 6/2014 | Manzke et al. |
| 2014/0180098 A1 | 6/2014 | Flaherty et al. |
| 2014/0188133 A1 | 7/2014 | Misener |
| 2014/0188440 A1 | 7/2014 | Donhowe et al. |
| 2014/0276059 A1 | 9/2014 | Sheehan |
| 2014/0276081 A1 | 9/2014 | Tegels |
| 2014/0276085 A1 | 9/2014 | Miller |
| 2014/0276690 A1 | 9/2014 | Grace |
| 2014/0343431 A1 | 11/2014 | Vajinepalli et al. |
| 2015/0005738 A1 | 1/2015 | Blacker |
| 2015/0011887 A1 | 1/2015 | Ahn et al. |
| 2015/0065916 A1 | 3/2015 | Maguire et al. |
| 2015/0073279 A1 | 3/2015 | Cai et al. |
| 2015/0112200 A1 | 4/2015 | Oberg et al. |
| 2015/0209113 A1 | 7/2015 | Burkholz et al. |
| 2015/0209526 A1 | 7/2015 | Matsubara et al. |
| 2015/0294497 A1 | 10/2015 | Ng et al. |
| 2015/0297097 A1 | 10/2015 | Matsubara et al. |
| 2015/0327841 A1 | 11/2015 | Banjanin et al. |
| 2015/0359991 A1 | 12/2015 | Dunbar et al. |
| 2016/0029995 A1 | 2/2016 | Navratil et al. |
| 2016/0029998 A1 | 2/2016 | Brister et al. |
| 2016/0100970 A1 | 4/2016 | Brister et al. |
| 2016/0101263 A1 | 4/2016 | Blumenkranz et al. |
| 2016/0113699 A1 | 4/2016 | Sverdlik et al. |
| 2016/0120607 A1 | 5/2016 | Sorotzkin et al. |
| 2016/0143622 A1 | 5/2016 | Xie et al. |
| 2016/0166232 A1 | 6/2016 | Merritt |
| 2016/0202053 A1 | 7/2016 | Walker et al. |
| 2016/0213398 A1 | 7/2016 | Liu |
| 2016/0278743 A1 | 9/2016 | Kawashima |
| 2016/0278869 A1 | 9/2016 | Grunwald |
| 2016/0296208 A1 | 10/2016 | Sethuraman et al. |
| 2016/0374644 A1 | 12/2016 | Mauldin, Jr. et al. |
| 2017/0079548 A1 | 3/2017 | Silverstein et al. |
| 2017/0086785 A1 | 3/2017 | Bjaerum |
| 2017/0164923 A1 | 6/2017 | Matsumoto |
| 2017/0172424 A1* | 6/2017 | Eggers ............... A61B 8/488 |
| 2017/0188839 A1 | 7/2017 | Tashiro |
| 2017/0196535 A1 | 7/2017 | Arai et al. |
| 2017/0215842 A1 | 8/2017 | Ryu et al. |
| 2017/0259013 A1 | 9/2017 | Boyden et al. |
| 2017/0265840 A1* | 9/2017 | Bharat ............... A61B 5/061 |
| 2017/0303894 A1 | 10/2017 | Scully |
| 2017/0367678 A1 | 12/2017 | Sirtori et al. |
| 2018/0015256 A1 | 1/2018 | Southard et al. |
| 2018/0116723 A1 | 5/2018 | Hettrick et al. |
| 2018/0125450 A1 | 5/2018 | Blackbourne et al. |
| 2018/0161502 A1 | 6/2018 | Nanan et al. |
| 2018/0199914 A1 | 7/2018 | Ramachandran et al. |
| 2018/0214119 A1 | 8/2018 | Mehrmohammadi et al. |
| 2018/0225993 A1 | 8/2018 | Buras et al. |
| 2018/0228465 A1 | 8/2018 | Southard et al. |
| 2018/0235576 A1 | 8/2018 | Brannan |
| 2018/0250078 A1 | 9/2018 | Shochat et al. |
| 2018/0272108 A1 | 9/2018 | Padilla et al. |
| 2018/0279996 A1 | 10/2018 | Cox et al. |
| 2018/0286287 A1 | 10/2018 | Razzaque |
| 2018/0310955 A1 | 11/2018 | Lindekugel et al. |
| 2018/0317881 A1 | 11/2018 | Astigarraga et al. |
| 2018/0366035 A1 | 12/2018 | Dunbar et al. |
| 2019/0060014 A1 | 2/2019 | Hazelton et al. |
| 2019/0069923 A1 | 3/2019 | Wang |
| 2019/0076121 A1 | 3/2019 | Southard et al. |
| 2019/0088019 A1 | 3/2019 | Prevrhal et al. |
| 2019/0105017 A1 | 4/2019 | Hastings |
| 2019/0117190 A1* | 4/2019 | Djajadiningrat ...... G06T 19/006 |
| 2019/0223757 A1 | 7/2019 | Durfee |
| 2019/0239850 A1 | 8/2019 | Dalvin et al. |

(56) References Cited

U.S. PATENT DOCUMENTS

| | | | |
|---|---|---|---|
| 2019/0282324 A1 | 9/2019 | Freeman et al. | |
| 2019/0298457 A1 | 10/2019 | Bharat | |
| 2019/0307516 A1 | 10/2019 | Schotzko et al. | |
| 2019/0339525 A1 | 11/2019 | Yanof et al. | |
| 2019/0355278 A1 | 11/2019 | Sainsbury et al. | |
| 2019/0365348 A1* | 12/2019 | Toume | A61B 8/065 |
| 2020/0041261 A1 | 2/2020 | Bernstein et al. | |
| 2020/0069285 A1 | 3/2020 | Annangi et al. | |
| 2020/0113540 A1 | 4/2020 | Gijsbers et al. | |
| 2020/0129136 A1 | 4/2020 | Harding et al. | |
| 2020/0188028 A1 | 6/2020 | Feiner et al. | |
| 2020/0230391 A1 | 7/2020 | Burkholz et al. | |
| 2021/0007710 A1* | 1/2021 | Douglas | A61B 8/469 |
| 2021/0045716 A1 | 2/2021 | Shiran et al. | |
| 2021/0166583 A1* | 6/2021 | Buras | G06F 3/011 |
| 2021/0307838 A1* | 10/2021 | Xia | A61B 34/20 |
| 2021/0353255 A1* | 11/2021 | Schneider | A61B 8/4254 |
| 2021/0402144 A1* | 12/2021 | Messerly | A61B 5/06 |
| 2022/0022969 A1 | 1/2022 | Misener | |
| 2022/0039685 A1 | 2/2022 | Misener et al. | |
| 2022/0039777 A1 | 2/2022 | Durfee | |
| 2022/0096797 A1 | 3/2022 | Prince | |
| 2022/0104886 A1 | 4/2022 | Blanchard et al. | |
| 2022/0117582 A1 | 4/2022 | McLaughlin et al. | |
| 2022/0160434 A1 | 5/2022 | Messerly et al. | |
| 2022/0168050 A1 | 6/2022 | Sowards et al. | |
| 2022/0172354 A1 | 6/2022 | Misener et al. | |
| 2022/0211442 A1 | 7/2022 | Mclaughlin et al. | |
| 2022/0381630 A1 | 12/2022 | Sowards et al. | |
| 2023/0113291 A1 | 4/2023 | de Wild et al. | |
| 2023/0240643 A1 | 8/2023 | Cermak et al. | |
| 2023/0389893 A1 | 12/2023 | Misener et al. | |
| 2024/0050061 A1 | 2/2024 | McLaughlin et al. | |
| 2024/0058074 A1 | 2/2024 | Misener | |
| 2024/0062678 A1 | 2/2024 | Sowards et al. | |

FOREIGN PATENT DOCUMENTS

| | | | |
|---|---|---|---|
| EP | 0933063 A1 | 8/1999 | |
| EP | 1504713 A1 | 2/2005 | |
| EP | 1591074 B1 | 5/2008 | |
| EP | 3181083 A1 | 6/2017 | |
| EP | 3530221 A1 | 8/2019 | |
| JP | 2000271136 A | 10/2000 | |
| JP | 2014150928 A | 8/2014 | |
| JP | 2018175547 A | 11/2018 | |
| KR | 20180070878 A | 6/2018 | |
| KR | 20190013133 A | 2/2019 | |
| WO | 2013059714 A1 | 4/2013 | |
| WO | 2014/115150 A1 | 7/2014 | |
| WO | 2014174305 A2 | 10/2014 | |
| WO | 2015/017270 A1 | 2/2015 | |
| WO | 2017096487 A1 | 6/2017 | |
| WO | 2017214428 A1 | 12/2017 | |
| WO | 2018/026878 A1 | 2/2018 | |
| WO | 2018134726 A1 | 7/2018 | |
| WO | 2018206473 A1 | 11/2018 | |
| WO | 2019/232451 A1 | 12/2019 | |
| WO | 2020/002620 A1 | 1/2020 | |
| WO | 2020/016018 A1 | 1/2020 | |
| WO | 2019/232454 A9 | 2/2020 | |
| WO | 2020/044769 A1 | 3/2020 | |
| WO | 2020102665 A1 | 5/2020 | |
| WO | 2020/186198 A1 | 9/2020 | |
| WO | 2022/031762 A1 | 2/2022 | |
| WO | 2022/072727 A2 | 4/2022 | |
| WO | 2022/081904 A1 | 4/2022 | |
| WO | 2022-203713 A2 | 9/2022 | |
| WO | WO-2022263763 A1 * | 12/2022 | |
| WO | 2023235435 A1 | 12/2023 | |
| WO | 2024010940 A1 | 1/2024 | |
| WO | 2024039608 A1 | 2/2024 | |
| WO | 2024039719 A1 | 2/2024 | |

OTHER PUBLICATIONS

U.S. Appl. No. 17/491,308, filed Sep. 30, 2021 Non-Final Office Action dated Jun. 5, 2023.
U.S. Appl. No. 17/501,909, filed Oct. 14, 2021 Non-Final Office Action dated Jun. 6, 2023.
U.S. Appl. No. 17/832,389, filed Jun. 3, 2022 Restriction Requirement dated Jul. 13, 2023.
U.S. Appl. No. 17/380,767, filed Jul. 20, 2021 Non-Final Office Action dated Mar. 6, 2023.
U.S. Appl. No. 17/393,283, filed Aug. 3, 2021 Non-Final Office Action dated Mar. 31, 2023.
U.S. Appl. No. 17/491,308, filed Sep. 30, 2021 Restriction Requirement dated Feb. 27, 2023.
PCT/US2021/050973 filed Sep. 17, 2021 International Search Report and Written Opinion dated Nov. 7, 2022.
U.S. Appl. No. 17/380,767, filed Jul. 20, 2021 Restriction Requirement dated Dec. 15, 2022.
U.S. Appl. No. 17/393,283, filed Aug. 3, 2021 Restriction Requirement dated Jan. 12, 2023.
U.S. Appl. No. 17/397,486, filed Aug. 9, 2021 Non-Final Office Action dated Jan. 23, 2023.
U.S. Appl. No. 17/501,909, filed Oct. 14, 2021 Restriction Requirement dated Feb. 1, 2023.
EZono, eZSimulator, https://www.ezono.com/en/ezsimulator/, last accessed Sep. 13, 2022.
Sonosim, https://sonosim.com/ultrasound-simulation/? last accessed Sep. 13, 2022.
U.S. Appl. No. 17/397,486, filed Aug. 9, 2021 Restriction Requirement dated Aug. 12, 2022.
Ikhsan Mohammad et al: "Assistive technology for ultrasound-guided central venous catheter placement", Journal of Medical Ultrasonics, Japan Society of Ultrasonics in Medicine, Tokyo, JP, vol. 45, No. 1, Apr. 19, 2017, pp. 41-57, XPO36387340, ISSN: 1346-4523, DOI: 10.1007/S10396-017-0789-2 [retrieved on Apr. 19, 2017].
Lu Zhenyu et al "Recent advances in 5 robot-assisted echography combining perception control and cognition." Cognitive Computation and Systems The Institution of Engineering and Technology, Michael Faraday House, Six Hills Way, Stevenage Herts. SG1 2AY UK vol. 2 No. 3 Sep. 2, 2020 (Sep. 2, 2020).
Pagoulatos, N et al. "New spatial localizer based on fiber optics with applications in 3D ultrasound imaging" Proceeding of Spie, vol. 3976 (Apr. 18, 2000; Apr. 18, 2000).
PCT/US2021/042369 filed Jul. 20, 2021 International Search Report and Written Opinion dated Oct. 25, 2021.
PCT/US2021/044419 filed Aug. 3, 2021 International Search Report and Written Opinion dated Nov. 19, 2021.
PCT/US2021/045218 filed Aug. 9, 2021 International Search Report and Written Opinion dated Nov. 23, 2021.
PCT/US2021/053018 filed Sep. 30, 2021 International Search Report and Written Opinion dated May 3, 2022.
PCT/US2021/055076 filed Oct. 14, 2021 International Search Report and Written Opinion dated Mar. 25, 2022.
Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docId/1235/file/SebastianVogtDissertation.pdf.
William F Garrett et al: "Real-time incremental visualization of dynamic ultrasound volumes using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.
PCT/US2023/024067 filed May 31, 2023 International Search Report and Written Opinion dated Sep. 15, 2023.
PCT/US2023/030160 filed Aug. 14, 2023 International Search Report and Written Opinion dated Oct. 23, 2023.
PCT/US2023/030347 filed Aug. 16, 2023 International Search Report and Written Opinion dated Nov. 6, 2023.
Practical guide for safe central venous catheterization and management 2017 Journal of Anesthesia vol. 34 published online Nov. 30, 2019 pp. 167-186.

(56) References Cited

OTHER PUBLICATIONS

State, A., et al. (Aug. 1996). Technologies for augmented reality systems: Realizing ultrasound-guided needle biopsies. In Proceedings of the 23rd annual conference on computer graphics and interactive techniques (pp. 439-446) (Year: 1996).
U.S. Appl. No. 17/380,767, filed Jul. 20, 2021 Notice of Allowance dated Aug. 31, 2023.
U.S. Appl. No. 17/393,283, filed Aug. 3, 2021 Final Office Action dated Oct. 16, 2023.
U.S. Appl. No. 17/397,486, filed Aug. 9, 2021 Advisory Action dated Oct. 5, 2023.
U.S. Appl. No. 17/397,486, filed Aug. 9, 2021 Final Office Action dated Aug. 4, 2023.
U.S. Appl. No. 17/491,308, filed Sep. 30, 2021 Board Decison dated Oct. 25, 2023.
U.S. Appl. No. 17/491,308, filed Sep. 30, 2021 Final Office Action dated Aug. 29, 2023.
U.S. Appl. No. 17/501,909, filed Oct. 14, 2021 Final Office Action dated Nov. 21, 2023.
U.S. Appl. No. 17/832,389, filed Jun. 3, 2022 Non-Final Office Action dated Oct. 6, 2023.
U.S. Appl. No. 17/491,308, filed Sep. 30, 2021 Non-Final Office Action dated Mar. 22, 2024.
U.S. Appl. No. 17/501,909, filed Oct. 14, 2021 Non-Final Office Action dated Mar. 21, 2024.
U.S. Appl. No. 17/832,389, filed Jun. 3, 2022 Advisory Action dated Apr. 4, 2024.
U.S. Appl. No. 17/832,389, filed Jun. 3, 2022 Notice of Allowance dated May 15, 2024.
U.S. Appl. No. 17/393,283, filed Aug. 3, 2021 Advisory Action dated Jan. 19, 2024.
U.S. Appl. No. 17/393,283, filed Aug. 3, 2021 Non-Final Office Action dated Feb. 29, 2024.
U.S. Appl. No. 17/397,486, filed Aug. 9, 2021 Non-Final Office Action dated Mar. 1, 2024.
U.S. Appl. No. 17/478,754, filed Sep. 17, 2021 Restriction Requirement dated Jan. 22, 2024.
U.S. Appl. No. 17/501,909, filed Oct. 14, 2021 Advisory Action dated Jan. 24, 2024.
U.S. Appl. No. 17/832,389, filed Jun. 3, 2022 Final Office Action dated Jan. 25, 2024.
U.S. Appl. No. 17/397,486, filed Aug. 9, 2021 Notice of Allowance dated Jul. 10, 2024.
U.S. Appl. No. 17/478,754, filed Sep. 17, 2021 Non-Final Office Action dated Jul. 1, 2024.
U.S. Appl. No. 17/491,308, filed Sep. 30, 2021 Notice of Allowance dated Jun. 27, 2024.
U.S. Appl. No. 17/501,909, filed Oct. 14, 2021 Final Office Action dated Aug. 5, 2024.

* cited by examiner

SYSTEMS AND METHODS FOR INTELLIGENT ULTRASOUND PROBE GUIDANCE

BACKGROUND

Ultrasound imaging is a widely accepted tool for guiding interventional instruments such as needles to targets such as blood vessels or organs in the human body. In order to successfully guide, for example, a needle to a blood vessel using ultrasound imaging, the needle is monitored in real-time both immediately before and after a percutaneous puncture in order to enable a clinician to determine the distance and the orientation of the needle to the blood vessel and ensure successful access thereto. However, through inadvertent movement of an ultrasound probe during the ultrasound imaging, the clinician can lose both the blood vessel and the needle, which can be difficult and time consuming to find again. In addition, it is often easier to monitor the distance and orientation of the needle immediately before the percutaneous puncture with a needle plane including the needle perpendicular to an image plane of the ultrasound probe. And it is often easier to monitor the distance and orientation of the needle immediately after the percutaneous puncture with the needle plane parallel to the image plane. As with inadvertently moving the ultrasound probe, the clinician can lose both the blood vessel and the needle when adjusting the image plane before and after the percutaneous puncture, which can be difficult and time consuming to find again. What is needed are ultrasound imaging systems and methods thereof that can dynamically adjust the image plane to facilitate guiding interventional instruments to targets in at least the human body.

Doppler ultrasound is a noninvasive approach to estimating the blood flow through your blood vessels by bouncing high-frequency sound waves (ultrasound) off circulating red blood cells. A doppler ultrasound can estimate how fast blood flows by measuring the rate of change in its pitch (frequency). Doppler ultrasound may be performed as an alternative to more-invasive procedures, such as angiography, which involves injecting dye into the blood vessels so that they show up clearly on X-ray images. Doppler ultrasound may help diagnose many conditions, including blood clots, poorly functioning valves in your leg veins, which can cause blood or other fluids to pool in your legs (venous insufficiency), heart valve defects and congenital heart disease, a blocked artery (arterial occlusion), decreased blood circulation into your legs (peripheral artery disease), bulging arteries (aneurysms), and narrowing of an artery, such as in your neck (carotid artery stenosis). Doppler ultrasound may also detect a direction of blood flow within a blood vessel.

SUMMARY

Disclosed herein is an ultrasound imaging system including an ultrasound probe including an array of ultrasonic transducers and an orientation system, wherein the ultrasonic transducers are configured to emit generated ultrasound signals into a patient, receive reflected ultrasound signals from the patient, and convert the reflected ultrasound signals into corresponding electrical signals of the ultrasound signals for processing into ultrasound images, and wherein the orientation system is configured to obtain orientation information of the ultrasound probe, a console configured to communicate with the ultrasound probe, the console including one or more processors and a non-transitory computer-readable medium having stored thereon logic, when executed by the one or more processors, causes operations including: obtaining the orientation information; performing an identification process on the ultrasound signals to identify an anatomical target (e.g., a target vessel); determining, based on the orientation information, a direction of movement required by the ultrasound probe to place the ultrasound probe at a predetermined position relative to the anatomical target (e.g., to center the ultrasound probe over the anatomical target); and initiating provision of feedback to a user of the ultrasound probe indicating the direction of movement required by the ultrasound probe to center the ultrasound probe over the anatomical target.

In some embodiments, the orientation information indicates positioning of the ultrasound probe on a Cartesian coordinate system relative to a skin surface of the patient. In some embodiments, the ultrasound probe includes an inertial measurement unit configured to obtain the orientation information. In some embodiments, the ultrasound probe includes an optical fiber having one or more of core fibers, wherein each of the one or more core 106s includes a plurality of sensors distributed along a longitudinal length of a corresponding core fiber and each sensor of the plurality of sensors is configured to (i) reflect a light signal of a different spectral width based on received incident light, and (ii) change a characteristic of the reflected light signal for use in determining a physical state of the optical fiber.

In some embodiments, the operations further include: providing a broadband incident light signal to the optical fiber, receiving a reflected light signal of the broadband incident light, wherein the reflected light signal is reflected from red blood cells within the patient body, and processing the reflected light signal to determine the orientation information. In some embodiments, the identification process includes applying a trained machine learning model configured to detect anatomical features within the ultrasound images and provide a bounding box around the anatomical target. In some embodiments, the provision of the feedback includes providing haptic feedback from a first side of the ultrasound probe, where the first side corresponds to the direction of movement required by the ultrasound probe to center the ultrasound probe over the anatomical target. In some embodiments, the system includes a needle including a second orientation system configured to obtain needle orientation information, and wherein the operations further include: determining, based on the needle orientation information, an orientation of the needle relative to the ultrasound probe, determining a trajectory of the needle, and generating a display screen illustrating the trajectory of the needle.

Also disclosed herein is a method of providing the ultrasound imaging system discussed above and providing instructions to cause performance of the operations also discussed above. Additionally, disclosed herein is a non-transitory, computer-readable medium having logic stored thereon that, when executed by a processor causes performance of the operations discussed above.

These and other features of the concepts provided herein will become more apparent to those of skill in the art in view of the accompanying drawings and following description, which describe particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which.

DESCRIPTION

Figure 1:
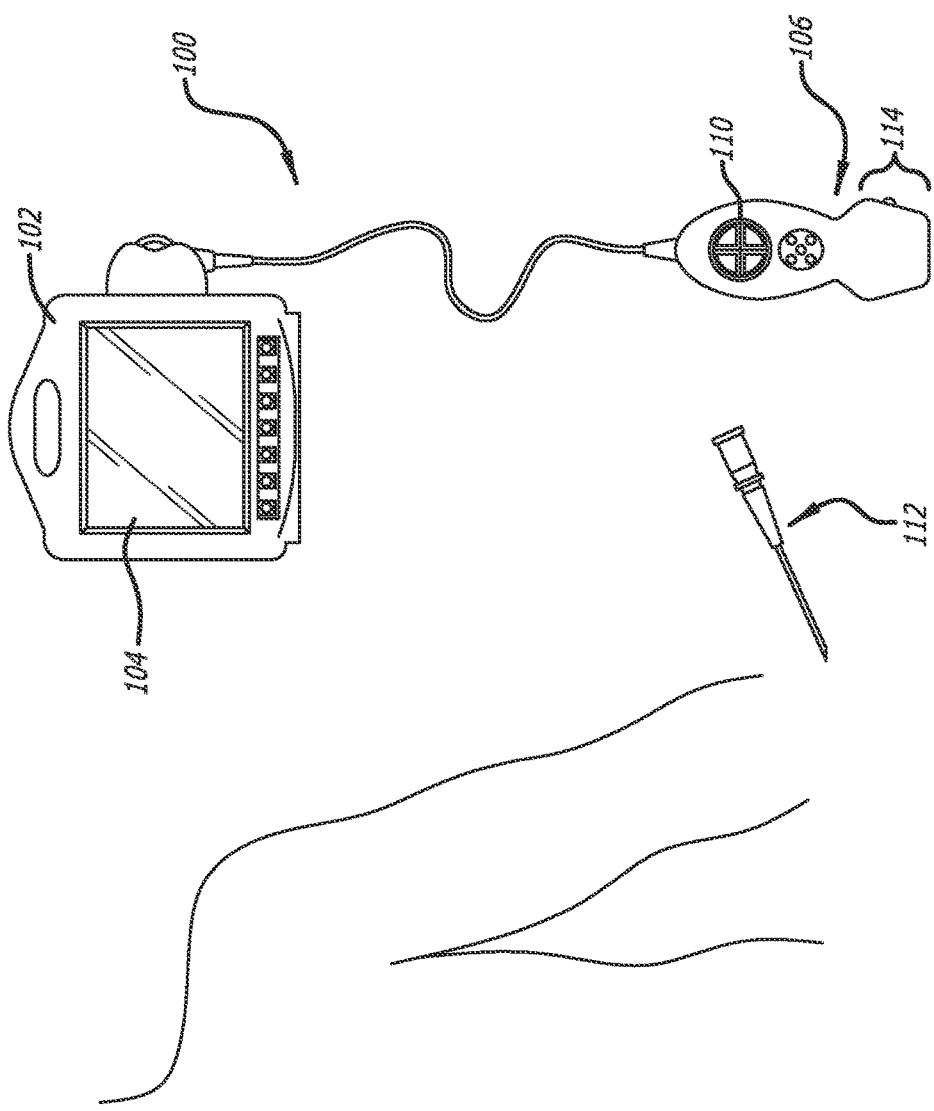
FIG. 1 illustrates an ultrasound imaging system and a patient in accordance with some embodiments.
Figure 1:
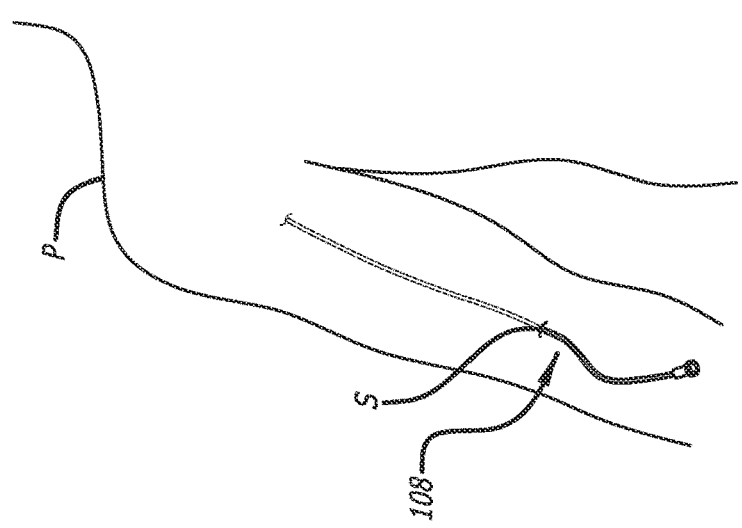

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, ultrasound imaging systems and methods thereof are needed that can dynamically adjust the image plane to facilitate guiding interventional instruments to targets in at least the human body. Disclosed herein are dynamically adjusting ultrasound imaging systems and methods thereof.

Figure 2:
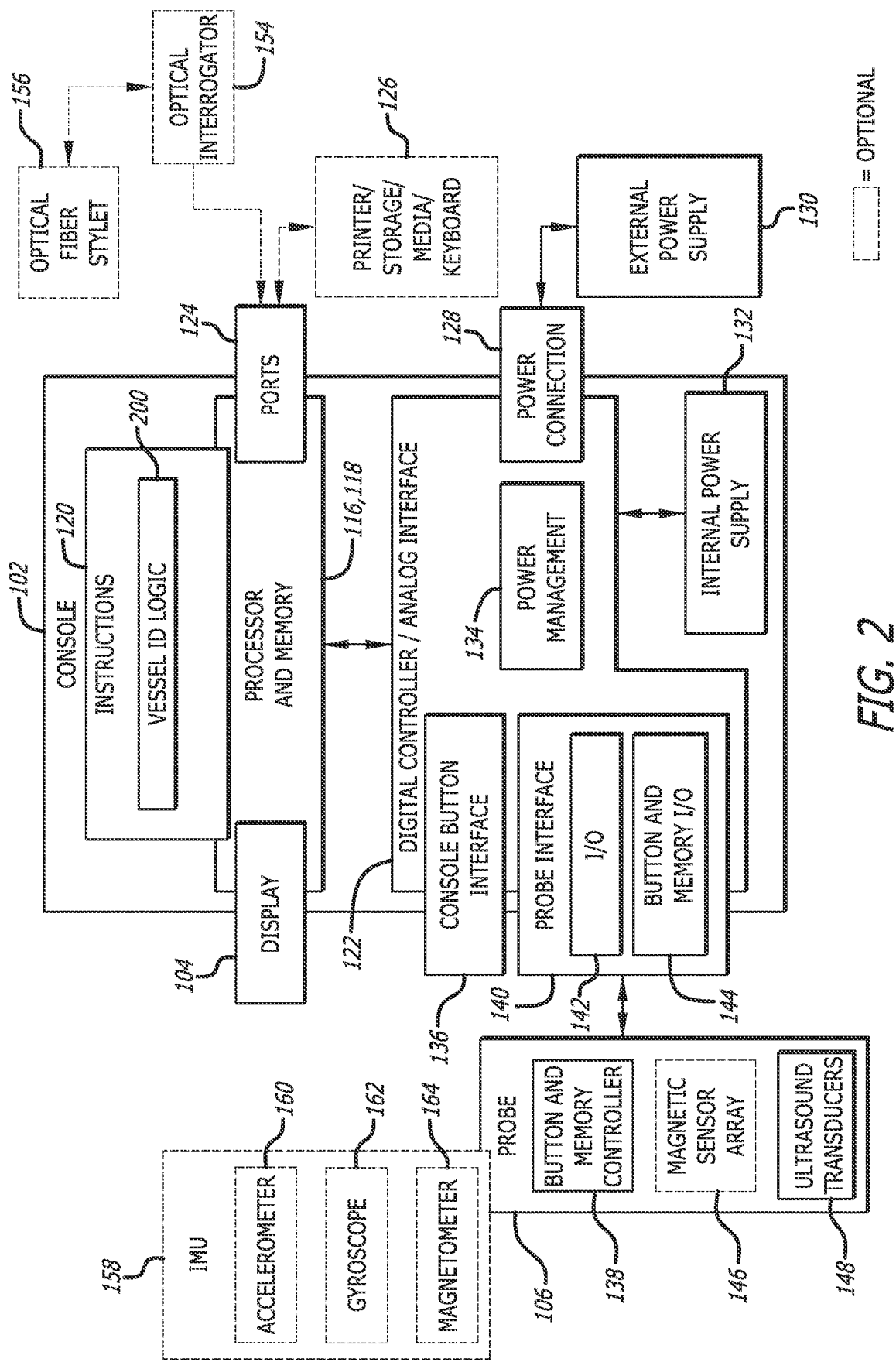
FIG. 2 illustrates a block diagram of a console of the ultrasound imaging system of FIG. 1 in accordance with some embodiments.

Referring now to FIG. 1, an ultrasound imaging system 100, a needle 112, and a patient P is shown in accordance with some embodiments. FIG. 2 illustrates a block diagram of the ultrasound imaging system 100 in accordance with some embodiments. The discussion below may be made with reference to both FIGS. 1-2. As shown, the ultrasound imaging system 100 includes a console 102, the display screen 104, and the ultrasound probe 106. The ultrasound imaging system 100 is useful for imaging a target such as a blood vessel or an organ within a body of the patient P prior to a percutaneous puncture with the needle 112 for inserting the needle 112 or another medical device into the target and accessing the target as well as imaging a target during the insertion process to provide confirmation of the needle 112. Indeed, the ultrasound imaging system 100 is shown in FIG. 1 in a general relationship to the patient P during a ultrasound-based medical procedure to place a catheter 108 into the vasculature of the patient P through a skin insertion site S created by a percutaneous puncture with the needle 112. It should be appreciated that the ultrasound imaging system 100 can be useful in a variety of ultrasound-based medical procedures other than catheterization. For example, the percutaneous puncture with the needle 112 can be performed to biopsy tissue of an organ of the patient P.

The console 102 houses a variety of components of the ultrasound imaging system 100, and it is appreciated the console 102 can take any of a variety of forms. A processor 116 and memory 118 such as random-access memory ("RAM") or non-volatile memory (e.g., electrically erasable programmable read-only memory ("EEPROM")) are included in the console 102 for controlling functions of the ultrasound imaging system 100. The processor may execute various logic operations or algorithms during operation of the ultrasound imaging system 100 in accordance with executable logic ("instructions") 120 stored in the memory 118 for execution by the processor 116. For example, the console 102 is configured to instantiate by way of the logic 120 one or more processes for dynamically adjusting a distance of activated ultrasonic transducers 148 from a predefined target (e.g., blood vessel) or area, an orientation of the activated ultrasonic transducers 148 to the predefined target or area, or both the distance and the orientation of the activated ultrasonic transducers 148 with respect to the predefined target or area, as well as process electrical signals from the ultrasound probe 106 into ultrasound images. Dynamically adjusting the activated ultrasonic transducers 148 uses ultrasound imaging data, magnetic-field data, shape-sensing data, or a combination thereof received by the console 102 for activating certain ultrasonic transducers of a 2-D array of the ultrasonic transducers 148 or moving those already activated in a linear array of the ultrasonic transducers 148. A digital controller/analog interface 122 is also included with the console 102 and is in communication with both the processor 116 and other system components to govern interfacing between the ultrasound probe 106 and other system components set forth herein.

The ultrasound imaging system 100 further includes ports 124 for connection with additional components such as optional components 126 including a printer, storage media, keyboard, etc. The ports 124 can be universal serial bus ("USB") ports, though other types of ports can be used for this connection or any other connections shown or described herein. A power connection 128 is included with the console 102 to enable operable connection to an external power supply 130. An internal power supply 132 (e.g., a battery) can also be employed either with or exclusive of the external power supply 130. Power management circuitry 134 is included with the digital controller/analog interface 122 of the console 102 to regulate power use and distribution.

The display screen 104 is integrated into the console 102 to provide a GUI and display information for a clinician during such as one-or-more ultrasound images of the target or the patient P attained by the ultrasound probe 106. In addition, the ultrasound imaging system 100 enables the distance and orientation of a magnetized medical device such as the needle 112 to be superimposed in real-time atop an ultrasound image of the target, thus enabling a clinician to accurately guide the magnetized medical device to the intended target. Notwithstanding the foregoing, the display screen 104 can alternatively be separate from the console 102 and communicatively coupled thereto. A console button interface 136 and control buttons 110 (see FIG. 1) included on the ultrasound probe 106 can be used to immediately call up a desired mode to the display screen 104 by the clinician for assistance in an ultrasound-based medical procedure. In some embodiments, the display screen 104 is an LCD device.

The ultrasound probe 106 is employed in connection with ultrasound-based visualization of a target such as a blood vessel (see FIG. 3A) in preparation for inserting the needle 112 or another medical device into the target. Such visualization gives real-time ultrasound guidance and assists in reducing complications typically associated with such insertion, including inadvertent arterial puncture, hematoma, pneumothorax, etc. As described in more detail below, the ultrasound probe 106 is configured to provide to the console 102 electrical signals corresponding to both the ultrasound imaging data, the magnetic-field data, the shape-sensing data, or a combination thereof for the real-time ultrasound guidance.

Optionally, a stand-alone optical interrogator 154 can be communicatively coupled to the console 102 by way of one of the ports 124. Alternatively, the console 102 can include an integrated optical interrogator integrated into the console 102. Such an optical interrogator is configured to emit input optical signals into a companion optical-fiber stylet 156 for shape sensing with the ultrasound imaging system 100, which optical-fiber stylet 156, in turn, is configured to be inserted into a lumen of a medical device such as the needle 112 and convey the input optical signals from the optical interrogator 154 to a number of FBG sensors along a length of the optical-fiber stylet 156. The optical interrogator 154 is also configured to receive reflected optical signals conveyed by the optical-fiber stylet 156 reflected from the number of FBG sensors, the reflected optical signals indicative of a shape of the optical-fiber stylet 156. The optical interrogator 154 is also configured to convert the reflected optical signals into corresponding electrical signals for processing by the console 102 into distance and orientation information with respect to the target for dynamically adjusting a distance of the activated ultrasonic transducers 148, an orientation of the activated ultrasonic transducers 148, or both the distance and the orientation of the activated ultrasonic transducers 148 with respect to the target or the medical device when it is brought into proximity of the target.

For example, the distance and orientation of the activated ultrasonic transducers 148 can be adjusted with respect to a blood vessel as the target. Indeed, an image plane can be established by the activated ultrasonic transducers 148 being perpendicular or parallel to the blood vessel in accordance with an orientation of the blood vessel. As used herein, the term "orientation information" may refer to the positioning of the probe 106 (or other medical instrument) in three dimensions relative to a fixed axis. In some embodiments, the fixed axis may refer to a perpendicular axis extending distally from a surface of a patient P (e.g., which may be representative of the Z-axis of a Cartesian coordinate system). Thus, orientation information of the probe 106 provides a geometric view of an angle of the ultrasound probe relative to the skin surface of patient P. Additionally, orientation information may provide an indication as to whether the ultrasound probe 106 is being held in a transverse or longitudinal orientation relative to a target vessel of the patient P.

FIG. 2 shows that the ultrasound probe 106 further includes a button and memory controller 138 for governing button and ultrasound probe 106 operation. The button and memory controller 138 can include non-volatile memory (e.g., EEPROM). The button and memory controller 138 is in operable communication with a probe interface 140 of the console 102, which includes an input/output ("I/O") component 142 for interfacing with the ultrasonic transducers 148 and a button and memory I/O component 144 for interfacing with the button and memory controller 138.

Also as seen in FIG. 2, the ultrasound probe 106 can include a magnetic-sensor array 146 for detecting a magnetized medical device such as the needle 112 during ultrasound-based medical procedures. The magnetic-sensor array 146 includes a number of magnetic sensors 150 embedded within or included on a housing of the ultrasound probe 106. The magnetic sensors 150 are configured to detect a magnetic field or a disturbance in a magnetic field as magnetic signals associated with the magnetized medical device when it is in proximity to the magnetic-sensor array 146. The magnetic sensors 150 are also configured to convert the magnetic signals from the magnetized medical device (e.g., the needle 112) into electrical signals for the console 102 to process into distance and orientation information for the magnetized medical device with respect to the predefined target, as well as for display of an iconographic representation of the magnetized medical device on the display screen 104. Thus, the magnetic-sensor array 146 enables the ultrasound imaging system 100 to track the needle 112 or the like.

Though configured here as magnetic sensors, it is appreciated that the magnetic sensors 150 can be sensors of other types and configurations. Also, though they are described herein as included with the ultrasound probe 106, the magnetic sensors 150 of the magnetic-sensor array 146 can be included in a component separate from the ultrasound probe 106 such as a sleeve into which the ultrasound probe 106 is inserted or even a separate handheld device. The magnetic sensors 150 can be disposed in an annular configuration about the probe head 114 of the ultrasound probe 106, though it is appreciated that the magnetic sensors 150 can be arranged in other configurations, such as in an arched, planar, or semi-circular arrangement.

Each magnetic sensor of the magnetic sensors 150 includes three orthogonal sensor coils for enabling detection of a magnetic field in three spatial dimensions. Such 3-dimensional ("3-D") magnetic sensors can be purchased, for example, from Honeywell Sensing and Control of Morristown, NJ. Further, the magnetic sensors 150 are configured as Hall-effect sensors, though other types of magnetic sensors could be employed. Further, instead of 3-D sensors, a plurality of 1-dimensional ("1-D") magnetic sensors can be included and arranged as desired to achieve 1-, 2-, or 3-D detection capability.

As shown in FIG. 2, the ultrasound probe 106 can further include an inertial measurement unit ("IMU") 158 or any one or more components thereof for inertial measurement selected from an accelerometer 160, a gyroscope 162, and a magnetometer 164 configured to provide positional-tracking data of the ultrasound probe 106 to the console 102 for stabilization of an image plane. The processor 116 is further configured to execute the logic 120 for processing the positional-tracking data for adjusting the distance of the activated ultrasonic transducers 148 from the target, the orientation of the activated ultrasonic transducers 148 to the target, or both the distance and the orientation of the activated ultrasonic transducers 148 with respect to the target to maintain the distance and the orientation of the activated ultrasonic transducers 148 with respect to the target when the ultrasound probe 106 is inadvertently moved with respect to the target.

It is appreciated that a medical device of a magnetizable material enables the medical device (e.g., the needle 112) to be magnetized by a magnetizer, if not already magnetized, and tracked by the ultrasound imaging system 100 when the magnetized medical device is brought into proximity of the magnetic sensors 150 of the magnetic-sensor array 146 or inserted into the body of the patient P during an ultrasound-based medical procedure. Such magnetic-based tracking of the magnetized medical device assists the clinician in placing a distal tip thereof in a desired location, such as in a lumen of a blood vessel, by superimposing a simulated needle image representing the real-time distance and orientation of the needle 112 over an ultrasound image of the body of the patient P being accessed by the magnetized medical device. Such a medical device can be stainless steel such as SS 304 stainless steel; however, other suitable needle materials that are capable of being magnetized can be employed. So configured, the needle 112 or the like can produce a magnetic field or create a magnetic disturbance in a magnetic field detectable as magnetic signals by the magnetic-sensor array 146 of the ultrasound probe 106 so as to enable the distance and orientation of the magnetized medical device to be tracked by the ultrasound imaging system 100 for dynamically adjusting the distance of the activated ultrasonic transducers 148, an orientation of the activated ultrasonic transducers 148, or both the distance and the orientation of the activated ultrasonic transducers 148 with respect to the magnetized medical device. In some embodiments, the needle 112 can be tracked using the teachings of one or more patents of U.S. Pat. Nos. 5,775,322; 5,879,297; 6,129,668; 6,216,028; and 6,263,230, each of which is incorporated by reference in its entirety into this application.

In some embodiments, the distance and orientation information determined by the ultrasound imaging system 100, together with an entire length of the magnetized medical device, as known by or input into the ultrasound imaging system 100, enables the ultrasound imaging system 100 to accurately determine the distance and orientation of the entire length of the magnetized medical device, including a distal tip thereof, with respect to the magnetic-sensor array 146. This, in turn, enables the ultrasound imaging system 100 to superimpose an image of the needle 112 on an ultrasound image produced by the ultrasound beam 152 of the ultrasound probe 106 on the display screen 104. For example, the ultrasound image depicted on the display screen 104 can include depiction of the surface of the skin of the patient P and a subcutaneous blood vessel thereunder to be accessed by the needle 112, as well as a depiction of the magnetized medical device as detected by the ultrasound imaging system 100 and its orientation to the vessel. The ultrasound image corresponds to an image acquired by the ultrasound beam 152 of the ultrasound probe 106. It should be appreciated that only a portion of an entire length of the magnetized medical device is magnetized and, thus, tracked by the ultrasound imaging system 100.

During operation of the ultrasound imaging system 100, the probe head 114 of the ultrasound probe 106 is placed against skin of the patient P. An ultrasound beam 152 is produced so as to ultrasonically image a portion of a target such as a blood vessel beneath a surface of the skin of the patient P. (See FIGS. 3A, 4A.) The ultrasonic image of the blood vessel can be depicted and stabilized on the display screen 104 of the ultrasound imaging system 100 as shown in FIGS. 3B, 4B despite inadvertent movements of the ultrasound probe 106. Note that further details regarding structure and operation of the ultrasound imaging system 100 can be found in U.S. Pat. No. 9,456,766, titled "Apparatus for Use with Needle Insertion Guidance System," which is incorporated by reference in its entirety into this application.

Figure 3A:
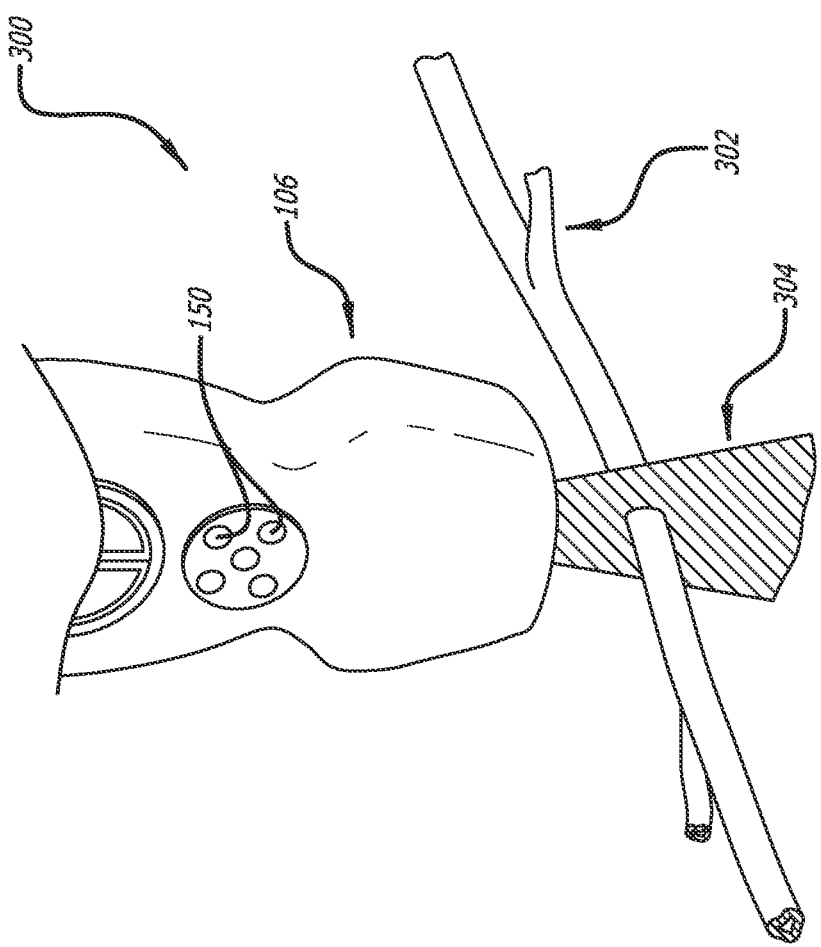
FIG. 3A illustrates the ultrasound probe 106 of the ultrasound imaging system 100 imaging a blood vessel of the patient P in an unsterile environment 300 prior to accessing the blood vessel in accordance with some embodiments.
Figure 3B:
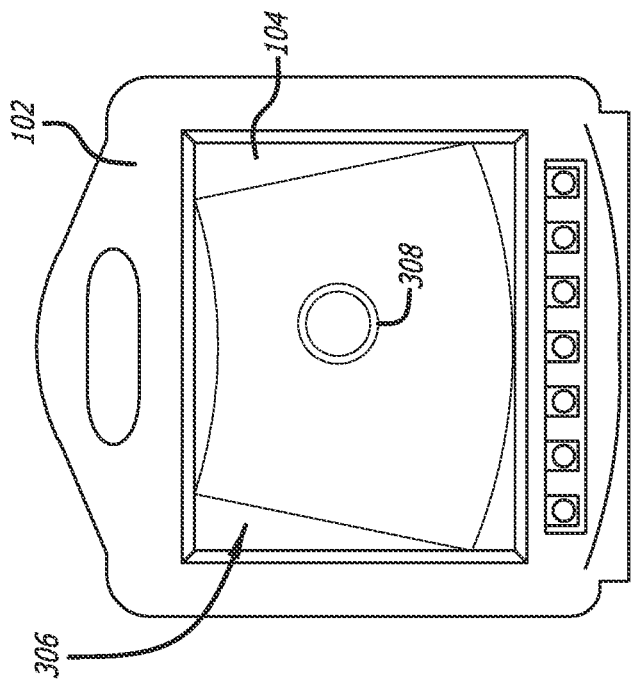
FIG. 3B illustrates an ultrasound image of the blood vessel of FIG. 3A on a display screen of the ultrasound imaging system in accordance with some embodiments.
Figure 4B:
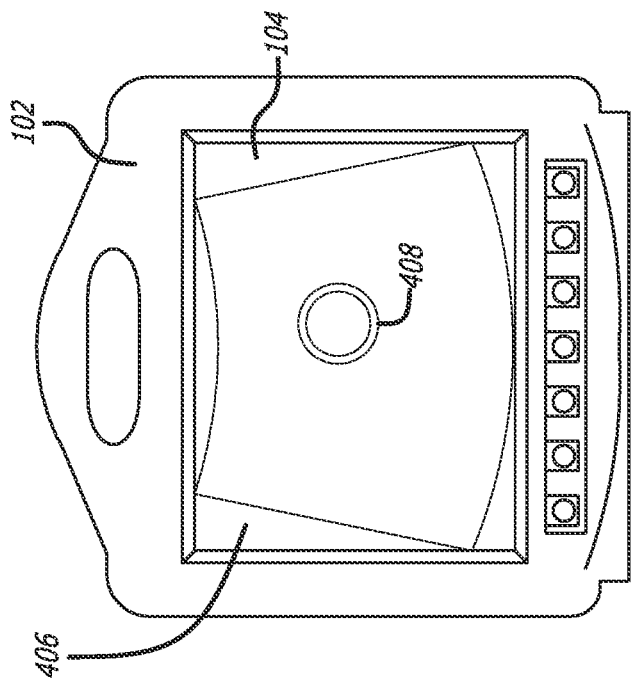
FIG. 4B illustrates an ultrasound image of the blood vessel of FIG. 4A on a display screen of the ultrasound imaging system in accordance with some embodiments.

FIG. 3A illustrates the ultrasound probe 106 of the ultrasound imaging system 100 imaging a blood vessel of the patient P in an unsterile environment 300 prior to accessing the blood vessel in accordance with some embodiments. The imaging performed in FIG. 3A may be referred to as pre-scan imaging. FIG. 3B illustrates an ultrasound image of the blood vessel of FIG. 3A (a "pre-scan image") 306 on a display screen 104 of the ultrasound imaging system 100 in accordance with some embodiments.

The pre-scan image 306 may be obtained at first time that is prior to preparing the patient P and the surrounding area for sterilization, where the pre-scan image 306 may be stored in the memory 118 of the console 102. The intended purpose of obtaining the pre-scan image 306 is to allow a clinician to obtain an image of the target vessel 302 using the ultrasound probe 106 without any constraints that may be imposed in order to maintain a sterile environment. As will be discussed below, the pre-scan image may then be used as a reference image to compare to the live scan image taken in a sterile field thereby allowing the clinician to confirm proper placement and orientation of the ultrasound probe 106.

In some embodiments, following operations to obtain, capture, and optionally to store, the pre-scan image, vessel identification logic 200 may be executed by the processor 116 causing performance of operations to identify a visual representation of the target vessel 302, such as the target vessel image 308 of FIG. 3B, within the pre-scan image 306 and/or detect other features of the pre-scan image 306. Other features detected may include those anatomical features typically visualized in an ultrasound image such as blood vessels, bones, muscles, tendons, ligaments, nerves, joints, etc.

The vessel identification logic 200 may be configured, upon execution by the processor 116, to cause performance of operations including computerized, automated analysis of the pre-scan image 306 to identify the target vessel image 308 through machine learning operations (e.g., application of a trained machine learning model). For instance, computerized, automated analysis may include operations comprising object recognition such as object detection methods, where the vessel identification logic 200 parses the pre-scan image 306 to locate a presence of one or more objects (e.g., the target vessel 302) with a bounding box and classify (label) the object within the bounding box. In order to perform such operations, the vessel identification logic 200 may include a machine learning model trained through supervised machine learning using a labeled data set. For example, a labeled data set may include ultrasound images that were previously captured ("historical data") that has also been labeled, e.g., by another trained machine learning model and/or by a subject matter expert. The machine learning model is then trained on the labeled historical data so that upon completion of the training, the machine learning model may detect objects within a new image (e.g., the pre-scan image 306 and a live scan image discussed below with respect to FIGS. 4A-4B), place bounding boxes around the images and classify the images. It is noted that is some embodiments, the classification step may be skipped such that the trained machine learning model is configured to output an image including bounding boxes around detected objects within the image.

Figure 4A:
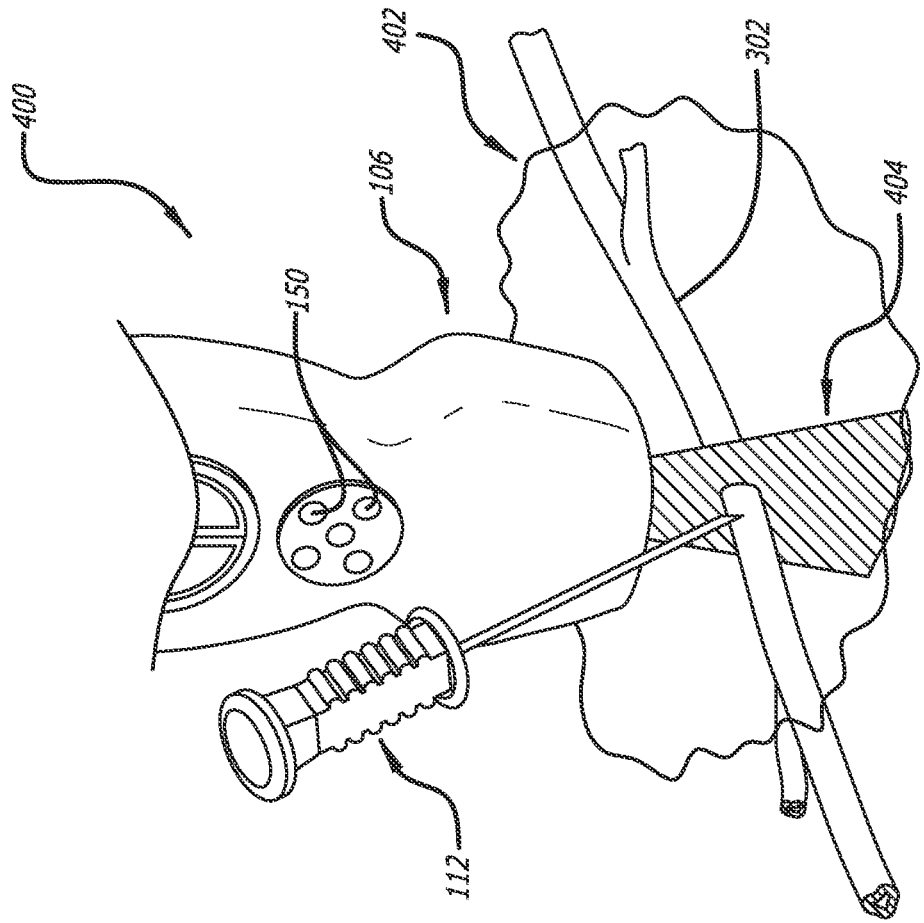
FIG. 4A illustrates the ultrasound probe of the ultrasound imaging system imaging a blood vessel of the patient P in a sterile environment prior to accessing and/or while accessing the blood vessel in accordance with some embodiments.

FIG. 4A illustrates the ultrasound probe 106 of the ultrasound imaging system 100 imaging a blood vessel of the patient P in a sterile environment 400 prior to accessing and/or while accessing the blood vessel in accordance with some embodiments. The imaging performed in FIG. 4A may be referred to as live scan imaging. FIG. 4B illustrates an ultrasound image of the blood vessel of FIG. 4A (a "live scan image") on a display screen 104 of the ultrasound imaging system 100 in accordance with some embodiments.

The live scan image 406 may be obtained at second time that is subsequent to creating a sterilized area 402 around an insertion site on the patient P (or generally an area on the patient P. The live scan image 406 may also be stored in the memory 118 of the console 102. As noted above, systems and methods disclosed herein may include obtaining a pre-scan image 306 with the intended purpose of allowing a clinician to use the pre-scan image 306 as a reference image to compare to the live scan image 406 (which is taken in a sterile field) thereby allowing the clinician to confirm proper placement and orientation of the ultrasound probe 106 during the live scan process, which may correspond to insertion of a medical device such as the needle 112.

In some embodiments, following operations to obtain, capture, and optionally to store, the live scan image 406, the vessel identification logic 200 may be executed by the processor 116 causing performance of operations to identify a visual representation of the target vessel 302, such as the target vessel image 308, within the live scan image 406 and/or detect other features of the live scan image 406. Other features detected may include those anatomical features typically visualized in an ultrasound image such as blood vessels, bones, muscles, tendons, ligaments, nerves, joints, etc.

Figure 5:
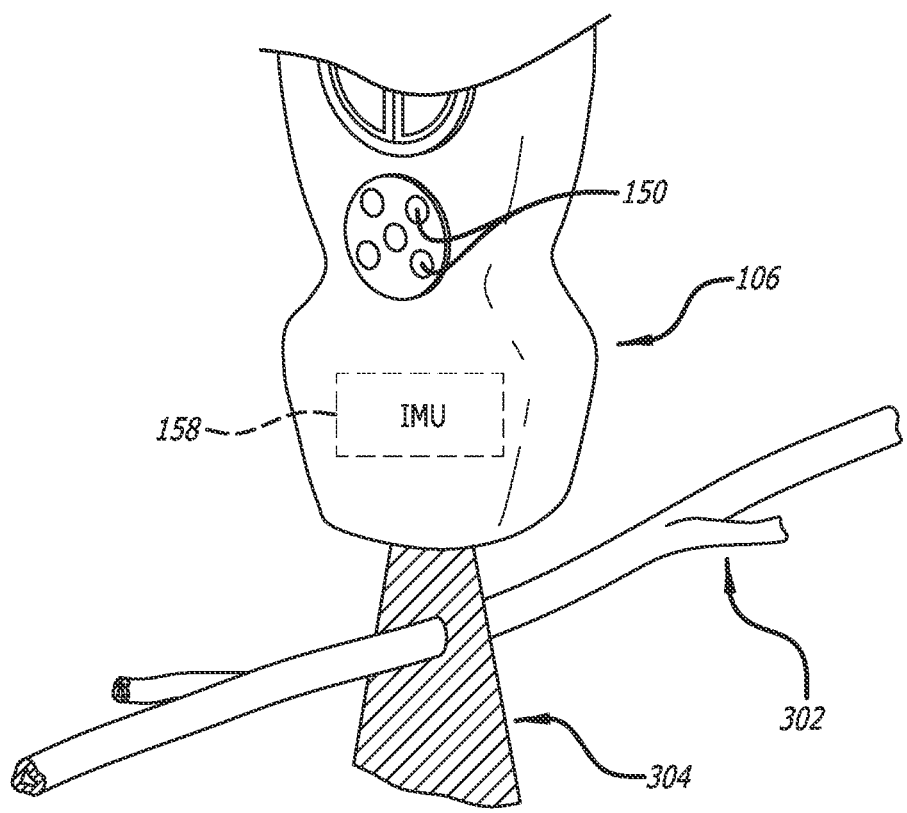
FIG. 5 illustrates the ultrasound probe 106 as illustrated in FIG. 3A that further includes an inertial measurement unit ("IMU") 158 in accordance with some embodiments.

Referring now to FIG. 5, the ultrasound probe 106 as illustrated in FIG. 3A that further includes an inertial measurement unit ("IMU") 158 is shown in accordance with some embodiments. As discussed above, the IMU 158 is configured to obtain inertial measurement from any of one or more components selected from an accelerometer 160, a gyroscope 162, and a magnetometer 164. Based on the obtained inertial measurements, the IMU 158 is configured to provide positional-tracking data of the ultrasound probe 106 to the console 102 thereby enabling spatial awareness of the probe 106. The processor 116 is further configured to execute the logic 120 for processing the positional-tracking data for adjusting the distance of the activated ultrasonic transducers 148 from the target, the orientation of the activated ultrasonic transducers 148 to the target, or both the distance and the orientation of the activated ultrasonic transducers 148 with respect to the target to maintain the distance and the orientation of the activated ultrasonic transducers 148 with respect to the target when the ultrasound probe 106 is inadvertently moved with respect to the target.

Figure 6A:
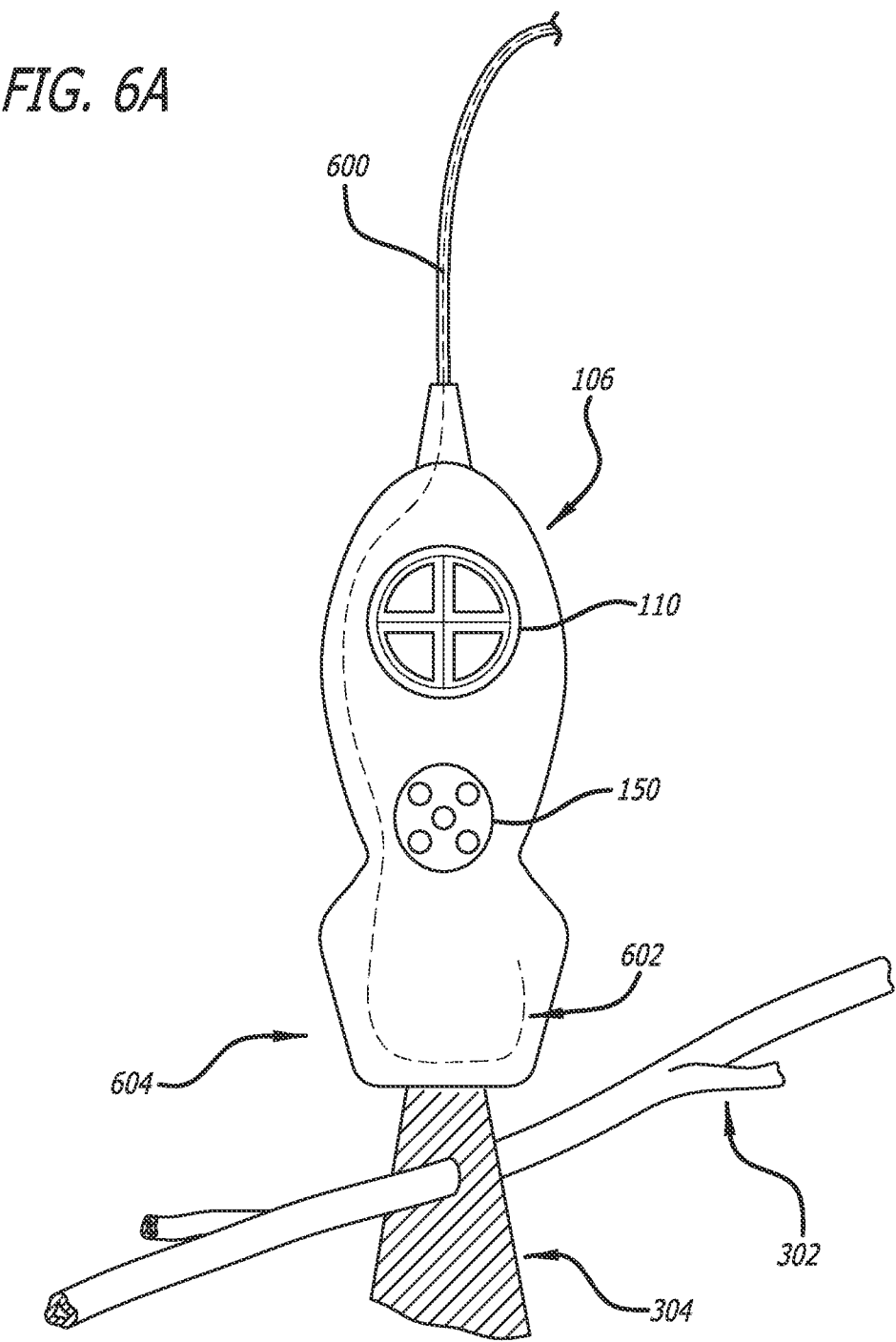
FIG. 6A illustrates the ultrasound probe 106 modified to include a multi-core optical fiber in accordance with some embodiments.

Referring to FIG. 6A, the ultrasound probe 106 modified to include a multi-core optical fiber is shown in accordance with some embodiments. The ultrasound probe 106 of FIG. 6A includes a multi-core optical fiber 600 that extends the length of a tether from the console 102 to the probe 106. Further, the multi-core optical fiber 600 may be configured in a predetermined geometry 602 at the distal end 604 of the probe 106. The predetermined geometry enables logic of the console 102 to perform shape sensing operations enabling detection of an orientation of the probe 106. More specifically, as the orientation of the predetermined geometry 602 relative to the transducers 148 is known prior to deployment of the probe 106, the ultrasound image displayed on the display 104 may be augmented with certain information, e.g., mirror coordination correction information, color-coding information, highlighting of a target vessel (see FIGS. 9A-9D), and the probe 106 may provide directional instructions via haptic feedback. Without knowing the orientation of the probe 106, such information cannot be provided.

Figure 6B:
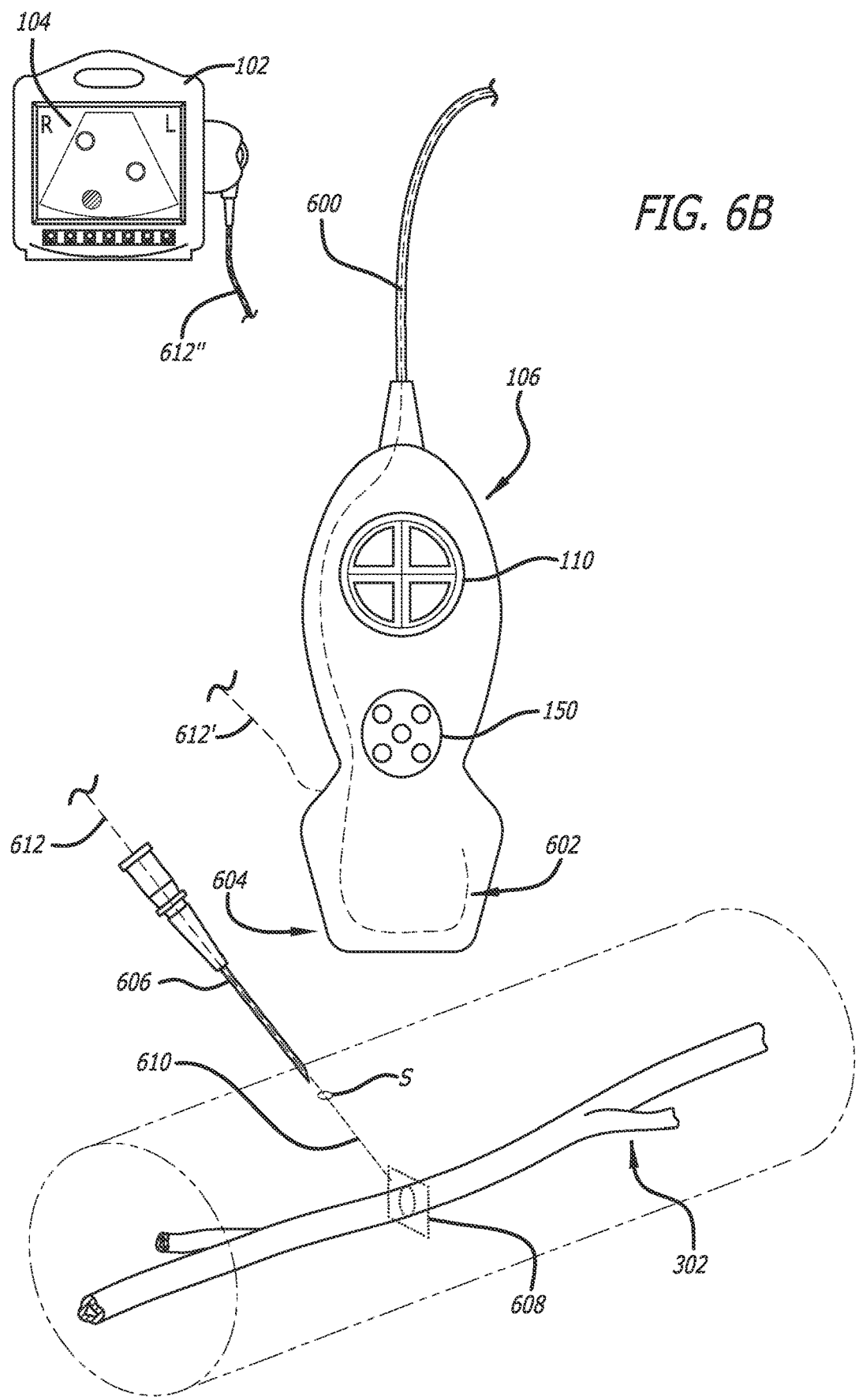
FIG. 6B illustrates the ultrasound probe 106 of FIG. 6A, a needle 606, and an exemplary needle trajectory in accordance with some embodiments.

Referring to FIG. 6B, the ultrasound probe 106 of FIG. 6A, a needle 606, and an exemplary needle trajectory is shown in accordance with some embodiments. FIG. 6B illustrates the probe 106 positioned on the skin surface of patient P in order to image the vessel 302. FIG. 6B further illustrates a needle 606 immediately adjacent an insertion site S intended to enter the target vessel 302 at a target site 608. Further, based on the orientation information obtained via the fiber optic data (e.g., reflected light signals returned from gratings disposed along the length of the multi-core optical fiber 600), logic of the console 102 may estimate a trajectory 610 of the needle 606. The trajectory 610 along with the ultrasound image (and/or a three-dimensional rendering of the vessel 302) may be displayed on the display 104.

In some embodiments, the needle may also include a multi-core optical fiber 612 that extends the length of the needle 606 from either the console 102 or the probe 106. In such embodiments, the orientation of the needle 606 may be determined based on a shape sensing of the multi-core optical fiber 612 extending through a tether to the probe 106 (optional multi-core optical fiber 612') or through a tether to the console 102 (optional multi-core optical fiber 612"). From the orientation of the probe 106 and the needle 606, a rendering of imaging captured by the probe 106, the target site 608, and the needle trajectory 610 may be generated and displayed on the display 104. Further, in addition to such information, knowledge of the human anatomy enables generation of a three-dimensional graphic for display on the display 104 (e.g., similar to the theoretical illustration of FIG. 6B).

As will be described below with respect to FIGS. 9A-9B, feedback may be provided to the clinician by the probe 106 in certain situations. For example, as discussed further below, the probe 106 may be configured to provide haptic feedback to the clinician indicating a direction to move the probe 106 in order to center the probe 106 over the target vessel 302 (and optionally over the insertion site 608). Certain feedback may also be provided by the probe 106 to instruct movement of the needle 606 (e.g., in any direction including yaw and/or pitch). The orientation of the needle may also be determined via the methodology discussed with respect to FIGS. 10A-12. For example, light emitting diodes (LEDs) on the probe (FIGS. 9A, 9D) may provide an indication of a direction to move the needle. Additional LEDs from those illustrated in FIGS. 9A, 9D may be included on the probe 106.

Figure 7:
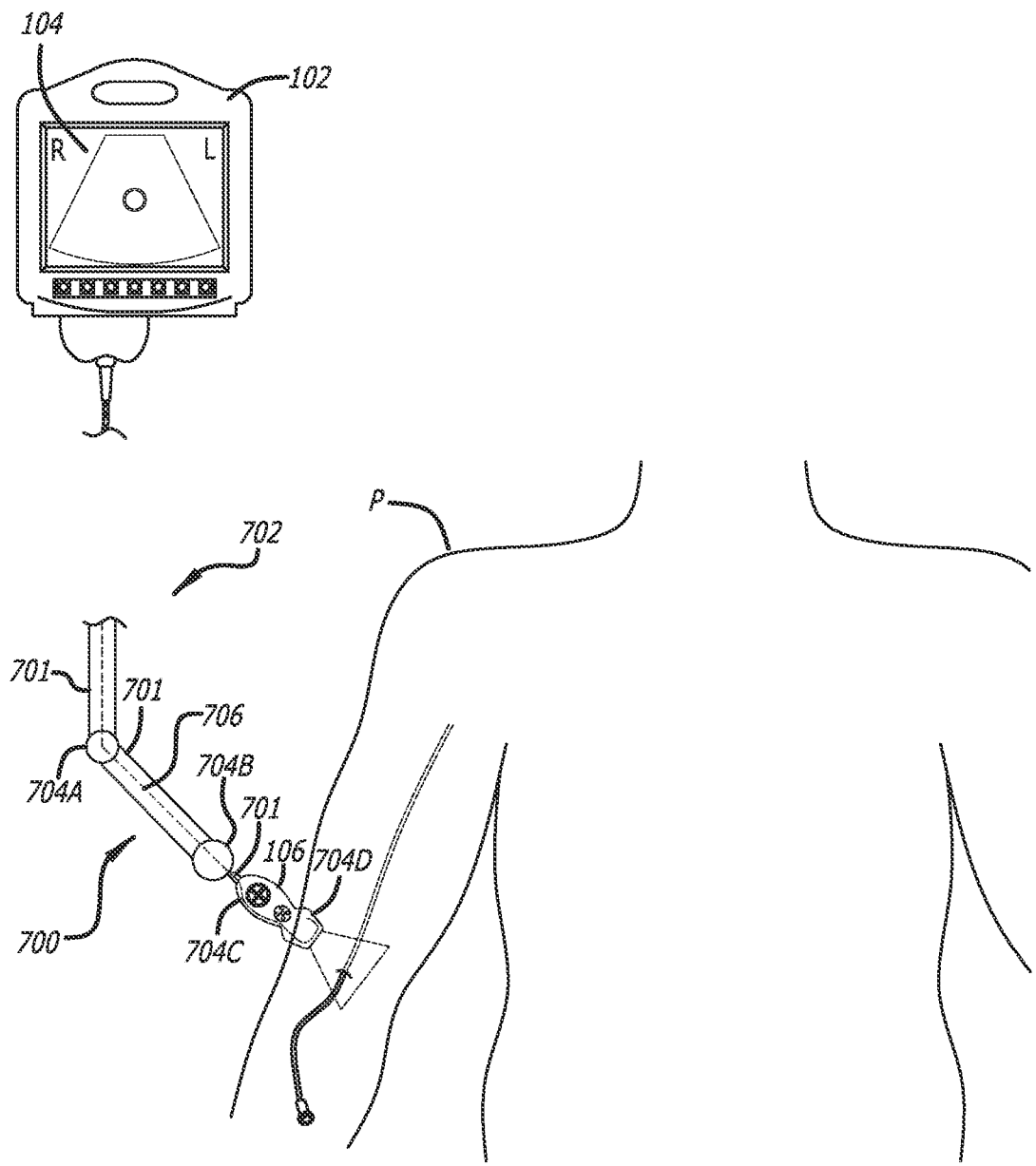
FIG. 7 illustrates the ultrasound probe 106 fixedly coupled to a mechanical arm 700 having a series of known location points along an arm length the patient P in accordance with some embodiments.

Referring to FIG. 7, the ultrasound probe 106 fixedly coupled to a mechanical arm 700 having a series of known location points along an arm length the patient P is shown in accordance with some embodiments. The mechanical arm 700 may be comprised of a series of arm components 701 and joints that hingedly couple the arm components 701 together with an ultrasound probe (e.g., the probe 106) fixed to the distal end of the most distal arm component. In some embodiments, a series of location points 704A-704D may be known, e.g., at each joint, at a proximal end of the probe 106, and at a distal end of the probe 106, such that an orientation and positioning of the mechanical arm 700 and the probe 106 may be determined relative to a fixed point, e.g., the console 102. In some embodiments, an optical fiber 706 (e.g., having one or more of core fibers) may extend from the console 102 to the probe 106, which provided reflected light signals to the console 102 thereby enabling determination of a positioning, orientation, and shape of the mechanical arm 700 and the probe 106 as detailed above. For instance, the optical fiber 706 may include the predetermined geometry 602 at the distal end of the probe 106 as illustrated in FIG. 6B in order to determine an orientation of the probe 106. The orientation, positioning, and configuration information obtained through the use of the mechanical arm 700 may be utilized in the same manner as that data obtained through the deployment of the IMU 158 within the probe 106 as discussed above.

Figure 8:
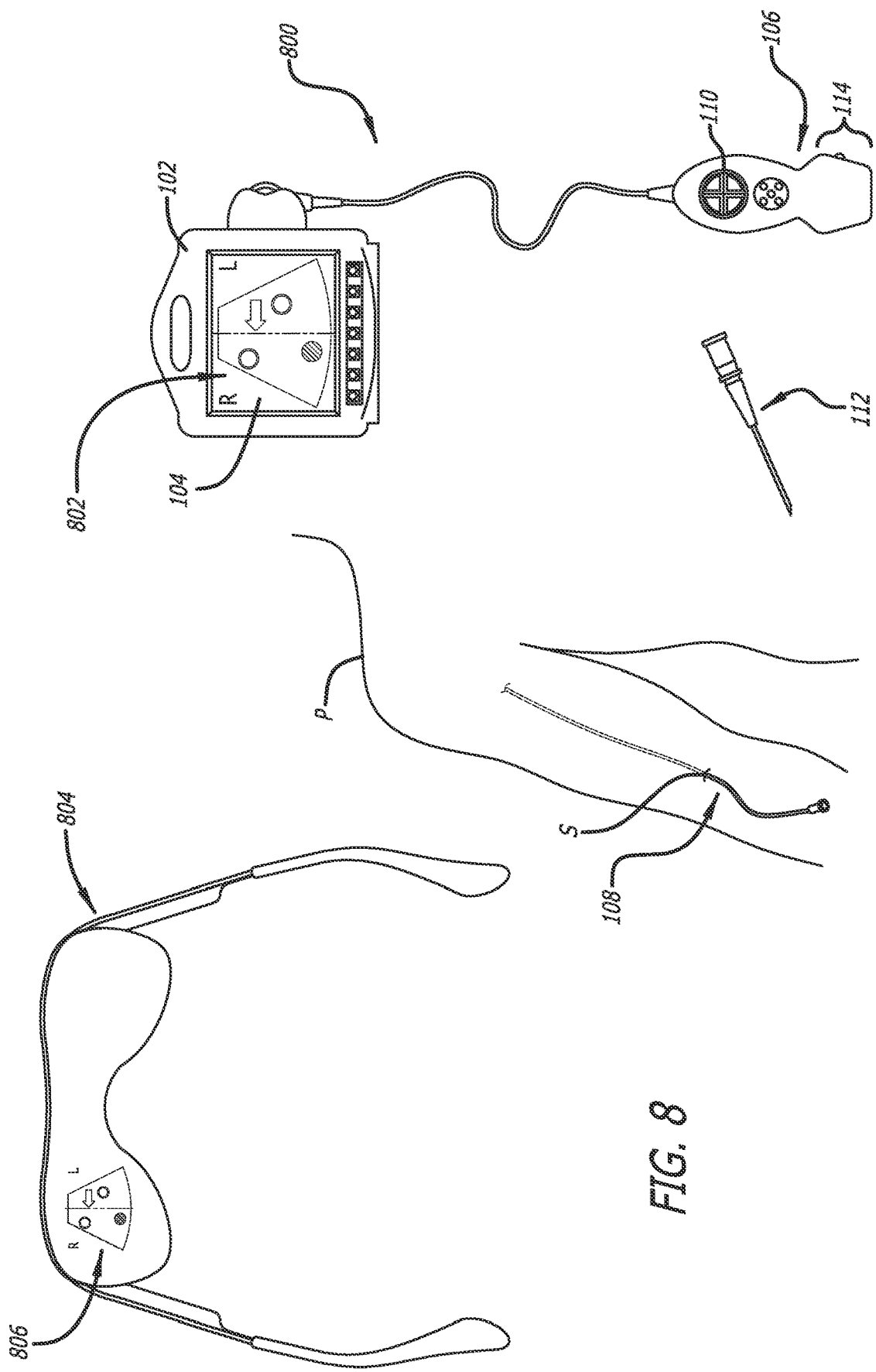
FIG. 8 illustrates an ultrasound imaging system 800 that includes alternative reality functionality in accordance with some embodiments.

Referring to FIG. 8, an ultrasound imaging system 800 that includes alternative reality functionality is shown in accordance with some embodiments. The ultrasound imaging system 800 includes many of the components of the ultrasound imaging system 100 of FIG. 1, where components that are held in common between the systems 100, 800 will not be discussed in detail. The system 800 includes the ability to perform augmented reality (AR) functionalities and components that provide AR data to a clinician. As used herein, the term "augmented reality" may refer to augmented reality (e.g., an enhancement of real-world images overlaid with computer-generated information) and virtual reality (e.g., replacement of a user's view with immersion within a computer-generated virtual environment).

For instance, the console may render an AR display screen 802 on the display 104. The AR display screen 802 may include certain visualizations as overlays on the ultrasound image obtained by the ultrasound probe 106. For example, the AR display screen 802 may include overlays that highlight certain anatomical features detected within the ultrasound image (e.g., vessels). In some embodiments, the target vessel may be distinguished visually from all detected anatomical features (e.g., the target vessel appears in a particular color, appears within a bounding box, etc.). Additional AR data that may be displayed includes directional indicators (e.g., "R"/"L" or "Right"/"Left") that assist the clinician in properly characterizing a mirror coordination of the ultrasound probe 106, when applicable. Further, a center line may be overlaid on the ultrasound image as well as an arrow that instructs the clinician as to a direction to move the ultrasound probe 106 in order to center the ultrasound probe 106 over a target vessel, which places the target vessel in the center of the ultrasound image displayed on the display 104. The disclosure is also intended to disclose positioning of the ultrasound probe 106 that are alternative to the center a target vessel (or anatomical target, e.g., an organ, a vessel blockage, a chamber within a heart or position within an organ, etc.). For instance, it may be advantageous to place the ultrasound probe at a particular distance from the center of the target vessel in order to allow a needle to properly access an insertion site.

Additionally, the system 800 includes an AR device 804 that provides secondary AR data as an alternative to the AR display screen 802. The AR device 804 provides a second option (e.g., modality) for viewing AR data, while the first and secondary AR data may the same or substantially the same. As illustrated in FIG. 8, the AR device 804 is represented by a pair of AR glasses 804 to be worn by a clinician performing the ultrasound procedure. The AR glasses 804 may be configured to display secondary AR data 806 on a display screen of the AR glasses 804. In the illustration of FIG. 8, the first and secondary AR data is substantially the same (e.g., substantially the same display). However, the secondary AR data 806 may be seen by the clinician as an overlay directly on the patient body. For example, when imaging the insertion site S, the clinician may view the insertion site S through the AR glasses 806 such that the ultrasound image including any of highlighting of detected anatomical features and/or directional or orientation markers also appear in an augmented manner. Thus, the clinician views the augmented ultrasound image directly on the patient body when viewing the patient body through the AR glasses 806. Advantageously, the AR glasses 806 enable the clinician to maintain eye contact on the imaging area of the patient body and the augmented ultrasound image may correct any mirrored coordination that would otherwise be present when viewing the ultrasound image on the display 104.

Figure 9A:
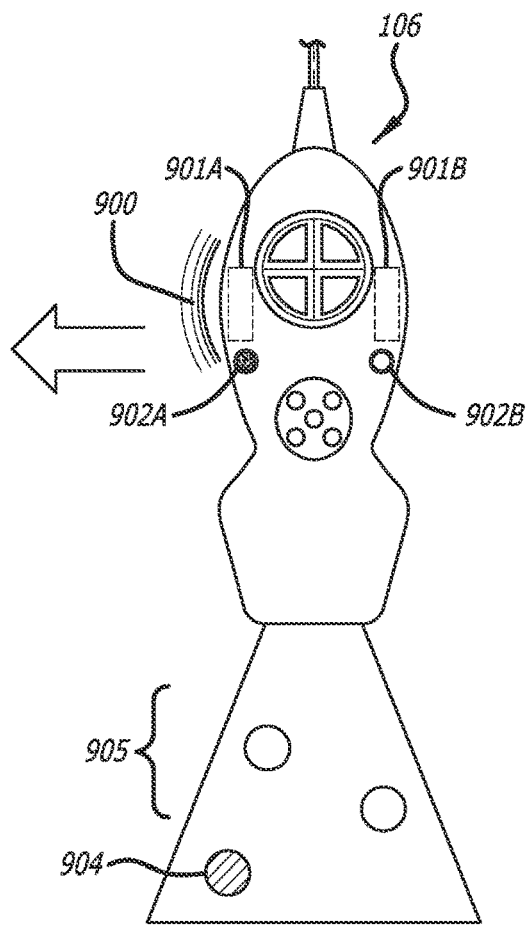
FIG. 9A illustrates the ultrasound probe 106 imaging a target vessel of the patient P and configured to provide feedback to a clinician that directs movement of the probe 106 center the probe 106 over the target vessel in accordance with some embodiments.

Referring now to FIG. 9A, the ultrasound probe 106 imaging a target vessel of the patient P and configured to provide feedback to a clinician that directs movement of the probe 106 center the probe 106 over the target vessel is shown in accordance with some embodiments. The probe 106 may be configured with vibration technology (e.g., actuators 901A-901B; linear resonant actuators (LRAs) or Piezoelectric actuators) that provide haptic feedback 900. Additionally, or in the alternative, the probe 106 may be configured with visual indicators (e.g., lights) configured to provide similar feedback by the actuators 901A-901B. The actuators 901A-901B may be activated to provide haptic feedback that instructs a clinician as to the direction move the probe 106 to center the probe 106 over the target vessel 904.

FIG. 9A illustrates a plurality of vessels: the target vessel 904; and secondary vessels 905 (e.g., non-target vessels). Thus, the console 102 may obtain an ultrasound image from the probe 106 and vessel identification logic 200 may perform a vessel identification process as discussed above to identify the target vessel 904 as well as detect the location of the target vessel 904 within the ultrasound image (e.g., relative to the ultrasound probe 106). The console 102 may then activate an actuator to provide haptic feedback instructing the clinician to move the probe 106 in a particular direction to center the probe 106 over the target vessel 904 (e.g., vibration on a right side of the probe 106 indicates the clinician move the probe 106 to the right). As a result, the clinician need not take his or her eyes off of the patient body and probe 106 to view the ultrasound image on the display 104 of the console 102 and determine which direction to move the probe 106. Similarly, the probe 106 may be configured with lights 902A, 902B that operate in the same manner as the actuators 901A, 901B (e.g., light up on a right side of the probe 106 indicates the clinician move the probe 106 to the right).

Figure 9B:
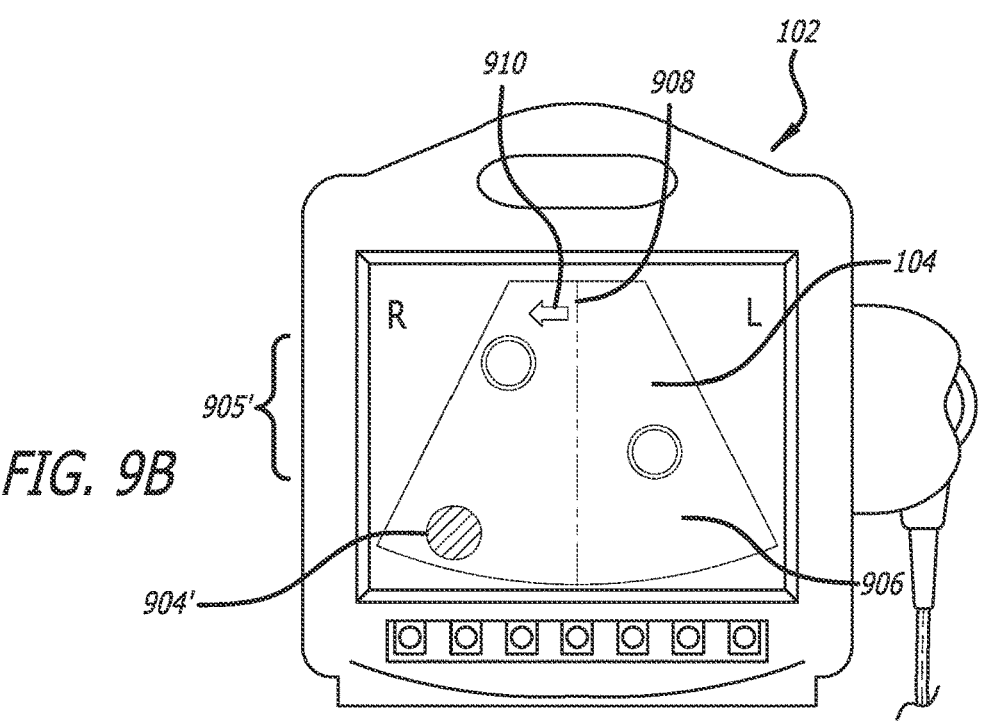
FIG. 9B is a first embodiment of a display screen illustrating the ultrasound imaging in real-time including a center line of the ultrasound probe 106 and a visual indication of a direction to move the probe 106 to center the probe 106 over the target vessel in accordance with some embodiments.

Referring to FIG. 9B, a first embodiment of a display screen illustrating the ultrasound imaging in real-time including a center line of the ultrasound probe 106 and a visual indication of a direction to move the probe 106 to center the probe 106 over the target vessel is shown in accordance with some embodiments. FIG. 9B illustrates a display screen 906 that may accompany, or be an alternative to, the feedback capabilities of the probe 106 discussed above. The display screen 906 may be rendered on the display 104 of the console 102 and illustrate an ultrasound image (or a portion) captured by the probe 106. The display screen 906 may include a visual indication of identified anatomical features (e.g., a target vessel image 904' and secondary vessel images 905') as well as a center line 908 and a directional arrow indicator 910, where the directional arrow indicator 910 instructs the clinician as to the direction to move the probe 106 in order to center the probe 106 over the target vessel 904.

Figure 9C:
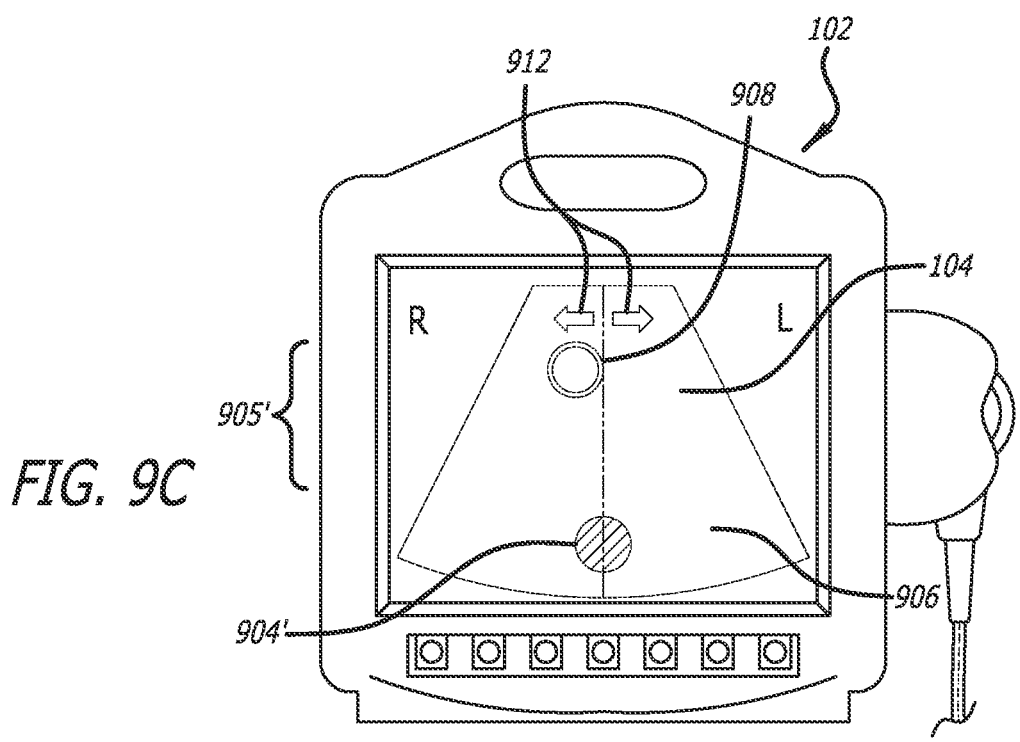
FIG. 9C is a second embodiment of a display screen illustrating the ultrasound imaging in real-time including a center line of the ultrasound probe 106 and a visual indication of a direction to move the probe 106 to center the probe 106 over the target vessel in accordance with some embodiments.

Referring to FIG. 9C, a second embodiment of a display screen illustrating the ultrasound imaging in real-time including a center line of the ultrasound probe 106 and a visual indication of a direction to move the probe 106 to center the probe 106 over the target vessel is shown in accordance with some embodiments. FIG. 9C provides an alternative to FIG. 9B where visual indicators provide explicit mirror coordination correction that may occur with ultrasound imaging. Thus, following identification of anatomical features (e.g., a target vessel 904 and secondary vessels 905), the console 102 may render the display screen 906 that includes a target vessel image 904' and a secondary vessel image 605' as well as a center line 908. Further, mirror coordination correction indicators 912 ("Right", "Left", and corresponding arrows) may be displayed, which indicate a direction to move the probe 106 in order to center the probe 106 over the target vessel 904 (or the secondary vessel 905). It is noted that the features illustrate in FIG. 9C may be combined with those of FIG. 9B.

Figure 9D:
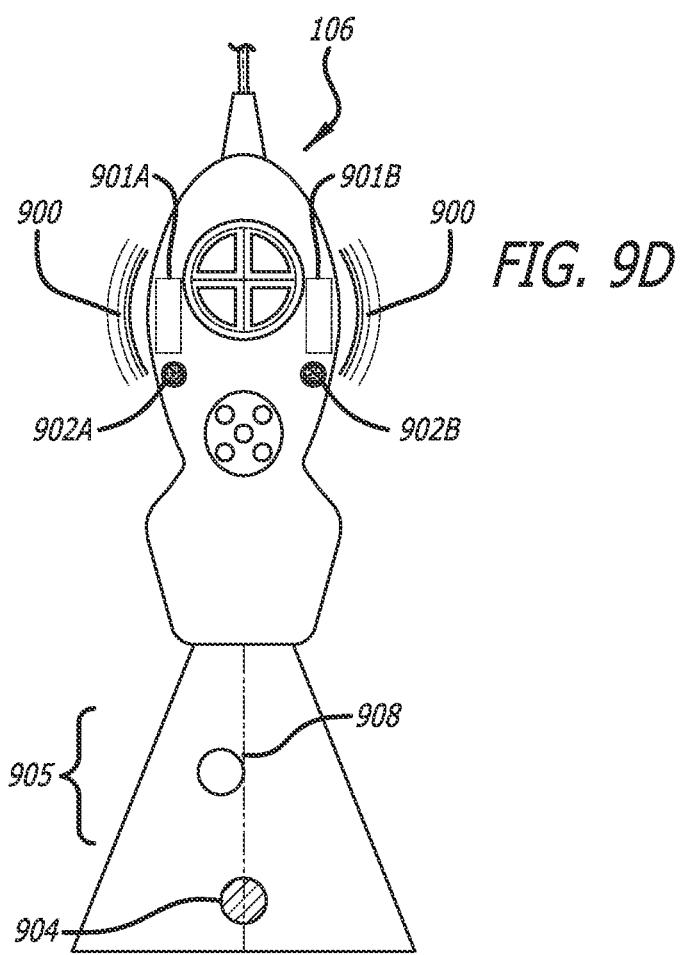
FIG. 9D illustrates the ultrasound probe 106 imaging a target vessel of the patient P and configured to provide feedback to a clinician when the probe 106 is centered over the target vessel in accordance with some embodiments.

Referring to FIG. 9D, the ultrasound probe 106 imaging a target vessel of the patient P and configured to provide feedback to a clinician when the probe 106 is centered over the target vessel is shown in accordance with some embodiments. FIG. 9D illustrates the probe 106 as discussed with respect to FIG. 9A while showing an embodiment of possible feedback when the probe 106 is centered over the target vessel 904. The center line 908 is shown in a dotted format merely to illustrate the center of the probe 106. In some embodiments, once the probe 106 is centered over the target vessel 904 (e.g., as determined by analysis of the ultrasound image by the vessel identification logic 200, and optionally in view of orientation and positioning data obtained via any of the modalities discussed above (e.g., shape sensing via a fiber optic, an IMU, etc.), feedback may be provided to the clinician that includes haptic feedback from both sides of the probe 106 and/or the lighting of both lights (e.g., light emitting diodes, LEDs) 902A, 902B. In some instances, the haptic feedback may differ from that provided when not centered over the target vessel 904 (e.g., when not centered, short pulses may be provided from a single side but when centered, one long pulse from both sides may be provided). Similarly, the lights 902A, 902B may blink in one situation and hold steady in another. Further, the feedback provided by the probe 106 may be customizable and/or dynamically adjusted prior to each use. For instance, any of the systems disclosed herein may be used within a medical facility (e.g., a hospital, a clinic, an urgent care facility, etc.) such that a plurality of clinicians may routinely utilize the console 102 and probe 106. In some embodiments, the console 102 may include the functionality for a clinician to sign-in to a particular profile, where each clinician profile stores a customized (or default) set of feedback.

Figure 10A:
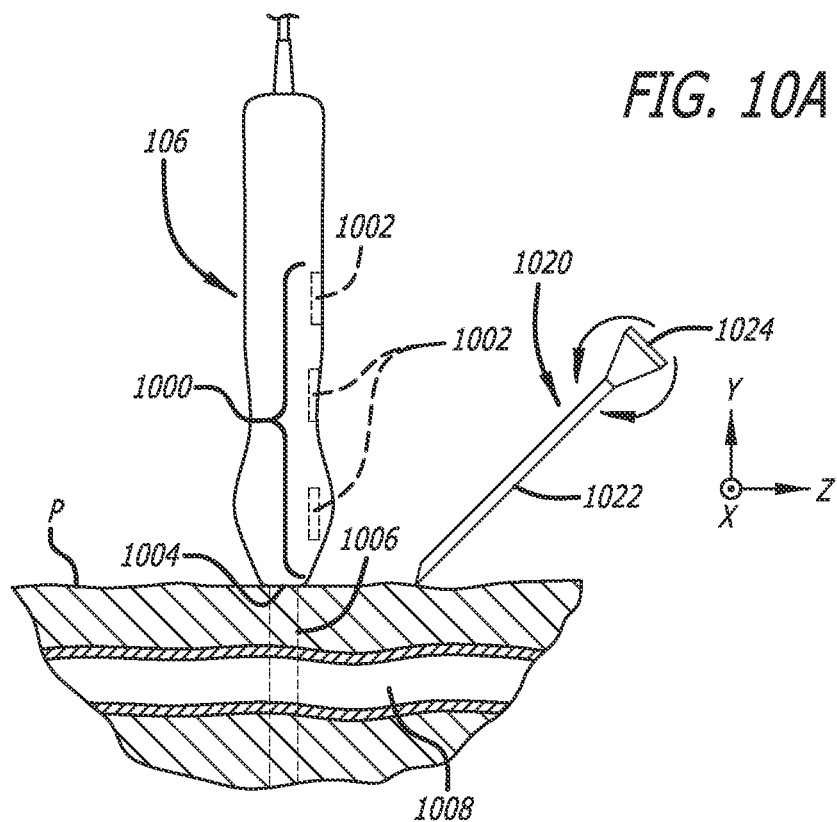
FIGS. 10A and 10B are simplified views of the ultrasound probe of the guidance system being used to guide a needle toward a vessel within the body of a patient in accordance with some embodiments.
Figure 10B:
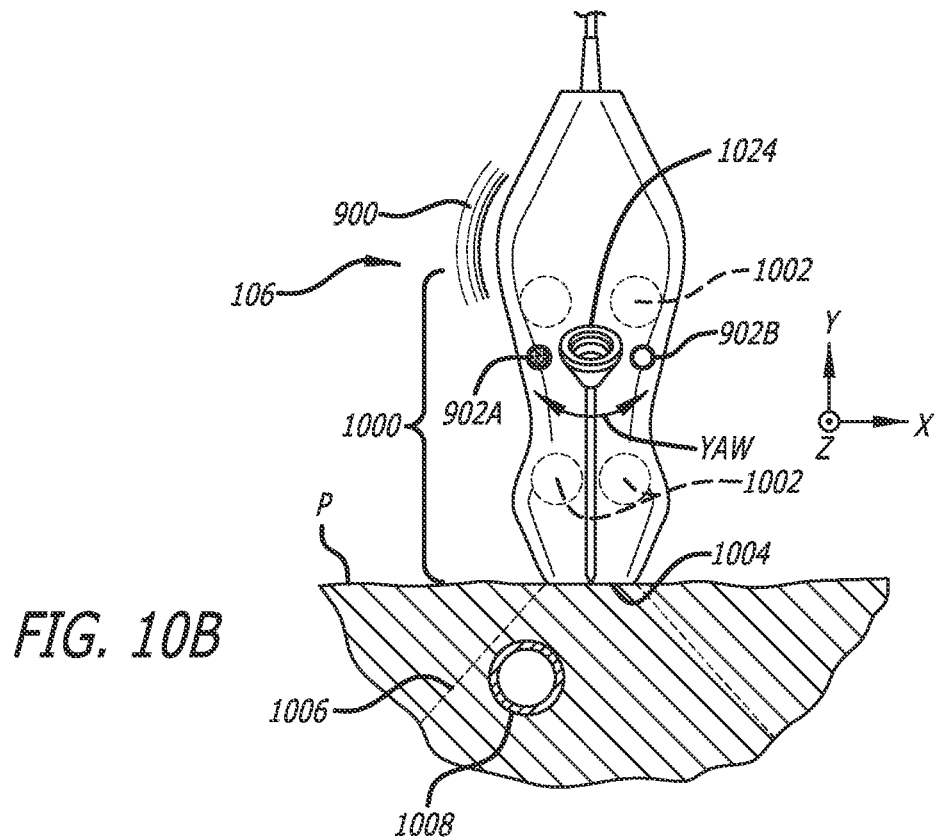

Referring to FIGS. 10A and 10B, simplified views of the ultrasound probe of the guidance system being used to guide a needle toward a vessel within the body of a patient are shown in accordance with some embodiments. FIGS. 10A-10B illustrate the ultrasound probe 106 of the system 100 and a needle 1020 (which may be included in system 100) in position and ready for insertion thereof through a skin surface of patient P to access a targeted internal body portion. In particular, the probe 106 is shown with its head 1004 placed against the patient skin and producing an ultrasound beam 1006 so as to ultrasonically image a portion of a vessel 1008 beneath the skin surface of patient P. The ultrasonic image of the vessel 1008 can be depicted on the display 104 of the console 102.

In the embodiment of FIGS. 10A-10B, the system 100 is configured to detect the position, orientation, and movement of the needle 1020. In particular, the sensor array 1000 of the probe 106 is configured to detect a magnetic field of the magnetic element 1024 included with the needle 1020. Each of the sensors 1002 of the sensor array 1000 is configured to spatially detect the magnetic element 1024 in three-dimensional space. Thus, during operation of the system 100 in accordance with the embodiment of FIGS. 10A-10B, magnetic field strength data of the needle's magnetic element 1024 sensed by each of the sensors 1002 is forwarded to a processor, such as the processor 116 of the console 102 (FIG. 2), which computes in real-time the position and/or orientation of the magnetic element 1024 Specifically, and as shown in FIGS. 10A-10B, the position of the magnetic element 1024 in X, Y, and Z coordinate space with respect to the sensor array 1000 can be determined by the system 100 using the magnetic field strength data sensed by the sensors 1002. Moreover, FIG. shows that the pitch of the magnetic element 1024 can also be determined, while FIG. 10B shows that the yaw of the magnetic element can be determined. Suitable circuitry of the probe 106, the console 120, or other component of the system can provide the calculations necessary for such position/orientation. In one embodiment, the magnetic element 1024 can be tracked using the teachings of one or more of the following U.S. Pat. Nos. 5,775,322; 5,879,297; 6,129,668; 6,216,028; 6,263,230; and 9,456,766. The contents of the aforementioned U.S. patents are incorporated herein by reference in their entireties.

The above position and orientation information determined by the system 100, together with the length of the canula 1022 and position of the magnetic element 1024 with respect to the distal needle tip as known by or input into the system, enable the system 100 to accurately determine the location and orientation of the entire length of the needle 1020 with respect to the sensor array 1000. Optionally, the distance between the magnetic element 1024 and the distal needle tip is known by or input into the system 100. This in turn enables the system 100 to superimpose an image of the needle 1020 on to an image produced by the ultrasound beam 1006 of the probe 106.

Figure 11A:
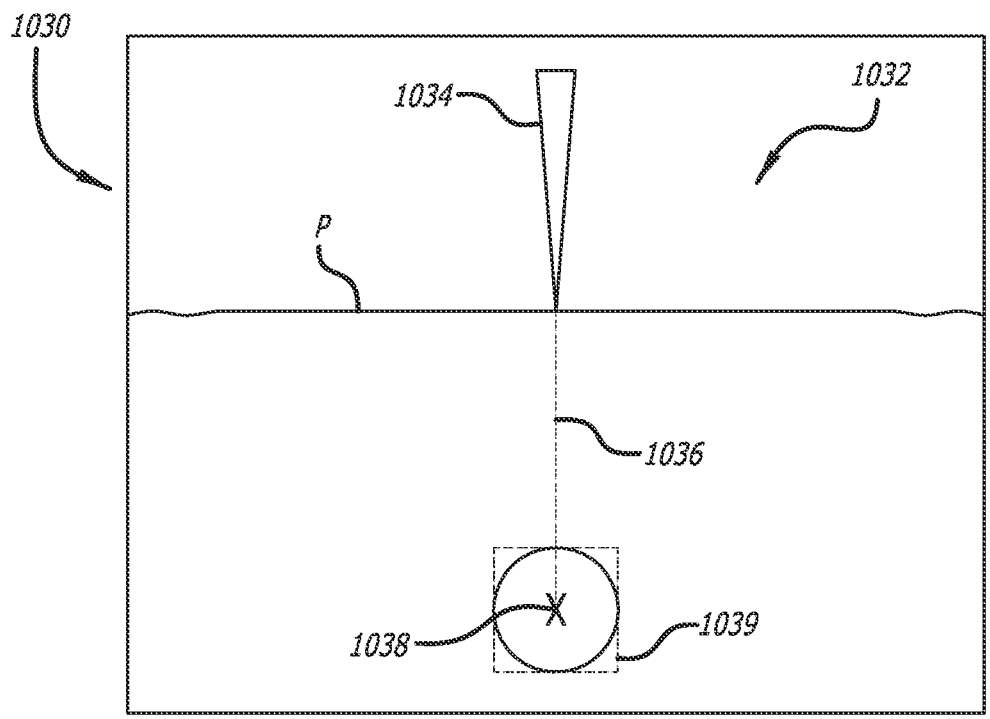
FIGS. 11A and 11B show possible screenshots for depiction on the display of the guidance system, showing the position and orientation of a needle in accordance with some embodiments.
Figure 11B:
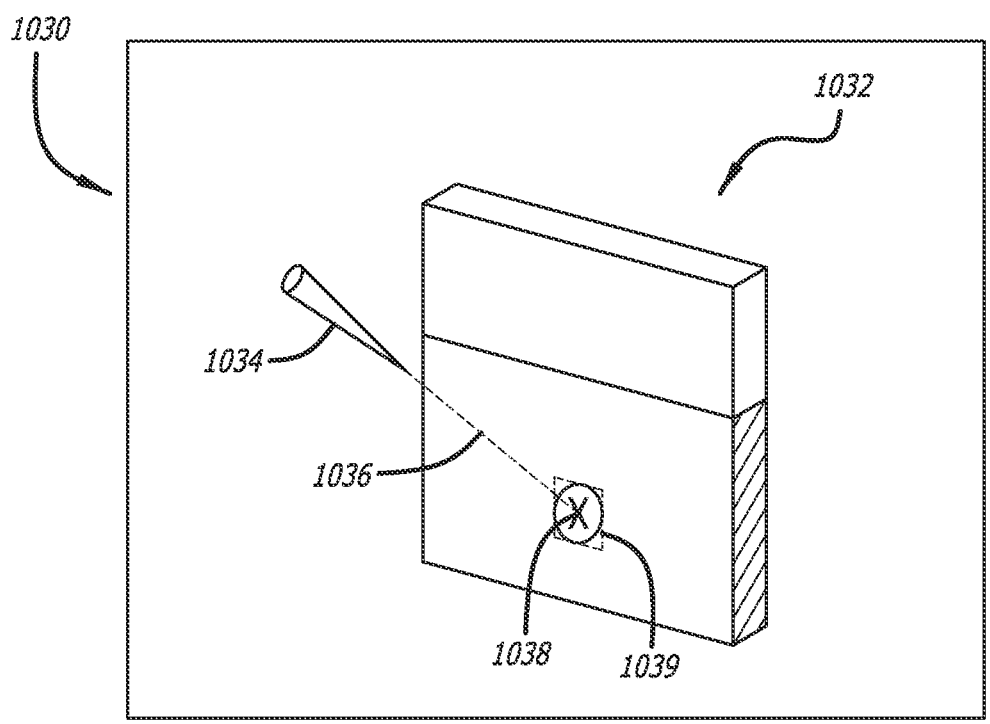

Referring now to FIGS. 11A and 11B, possible screenshots for depiction on the display of the guidance system, showing the position and orientation of a needle are shown in accordance with some embodiments. FIGS. 11A and 11B show examples of a superimposition of the needle onto an ultrasound image. Specifically, FIGS. 11A and 11B each show a screenshot 1030 that can be depicted on the display 104 of the console 102, for instance. In FIG. 11A, an ultrasound image 1032 is shown, including depiction of the skin surface of patient P, and the subcutaneous vessel 1008 (area 1039). The ultrasound image 1032 corresponds to an image acquired by the ultrasound beam 1006 shown in FIGS. 11A and 11B, for instance. The screenshot 1030 further shows a needle image 1034 representing the position and orientation of the actual needle 1020 as determined by the system 100 as described above. Because the system is able to determine the location and orientation of the needle 1020 with respect to the sensor array 1000, the system is able to accurately determine the position and orientation of the needle 1020 with respect to the ultrasound image 1032 and superimpose it thereon for depiction as the needle image 1034 on the display 104. Coordination of the positioning of the needle image 1034 on the ultrasound image 1032 is performed by suitable algorithms executed by the processor 116 or other suitable component of the system 100.

Specifically, FIG. 11A shows that in one embodiment the system 100 can depict a projected path 1036 based on the current position and orientation of the needle 1020 as depicted by the needle image 1034. The projected path 1036 assists a clinician in determining whether the current orientation of the needle 1020, as depicted by the needle image 1034 on the display 104, will result in arriving at the desired internal body portion target, such as the vessel 1008. Again, as the orientation and/or position of the needle image 1034 changes, the projected path 1036 is correspondingly modified by the system 100. FIG. 11B shows that, in one embodiment, the screenshot 1030 can be configured such that the ultrasound image 1032 and the needle image 1034 are oriented so as to be displayed in a three-dimensional aspect. This enables the angle and orientation of the needle 1020, as depicted by the needle image 1034, to be ascertained and compared with the intended target imaged by the ultrasound image 1032. It should be noted that the screenshots 1030 are merely examples of possible depictions produced by the system 100 for display. Also, it is appreciated that, in addition to the visual display 104, aural information, such as beeps, tones, etc., can also be employed by the system 100 to assist the clinician during positioning and insertion of the needle into the patient. Further, haptic feedback may be provided to the clinician via the probe 106 in a similar manner as discussed above with respect to at least FIGS. 9A-9D.

Further details are given here regarding use of the system 100 in guiding a needle or other medical device in connection with ultrasonic imaging of a targeted internal body portion ("target") of a patient, according to one embodiment. With the magnetic element-equipped needle 1020 positioned a suitable distance (e.g., two or more feet) away from the ultrasound probe 106 including the sensor array 1000, the probe is employed to ultrasonically image, for depiction on the display 104 of the system 100, the target within the patient that the needle is intended to intersect via percutaneous insertion. Following a calibration of the system 100 and obtaining or determining a total length of the needle 1020, and/or position of the magnetic element with respect to the distal needle tip such as by user input, automatic detection, or in another suitable manner, the needle 1020 is then brought into the range of the sensors 1002 of the sensor array 1000 of the probe 106. Each of the sensors 1002 detects the magnetic field strength associated with the magnetic element 1024 of the needle 1020, which data is forwarded to the processor 116. As the sensors 1002 detect the magnetic field, algorithms are performed by the processor 116 to calculate a magnetic field strength of the magnetic element 1024 of the needle 1020 at predicted points in space in relationship to the probe. The processor 116 then compares the actual magnetic field strength data detected by the sensors 1002 to the calculated field strength values (detail of this process is further described by the U.S. patents identified above). This process can be iteratively performed until the calculated value for a predicted point matches the measured data. Once this match occurs, the magnetic element 1024 has been positionally located in three-dimensional space. Using the magnetic field strength data as detected by the sensors 1002, the pitch and yaw (i.e., orientation) of the magnetic element 1024 can also be determined. Together with the known length of the needle 1020 and the position of the distal tip of the needle with respect to the magnetic element, this enables an accurate representation of the position and orientation of the needle can be made by the system 100 and depicted as a virtual model, i.e., the needle image 1034, on the display 104. Note that the predicted and actual detected values must match within a predetermined tolerance or confidence level in one embodiment for the system 100 to enable needle depiction to occur. Further detail as to the guidance of a needle toward a vessel within the body of a patient as discussed with respect to FIGS. 10A-12 is provided in U.S. Pat. No. 9,456,766, the entire contents of which is incorporated herein by reference.

Figure 12:
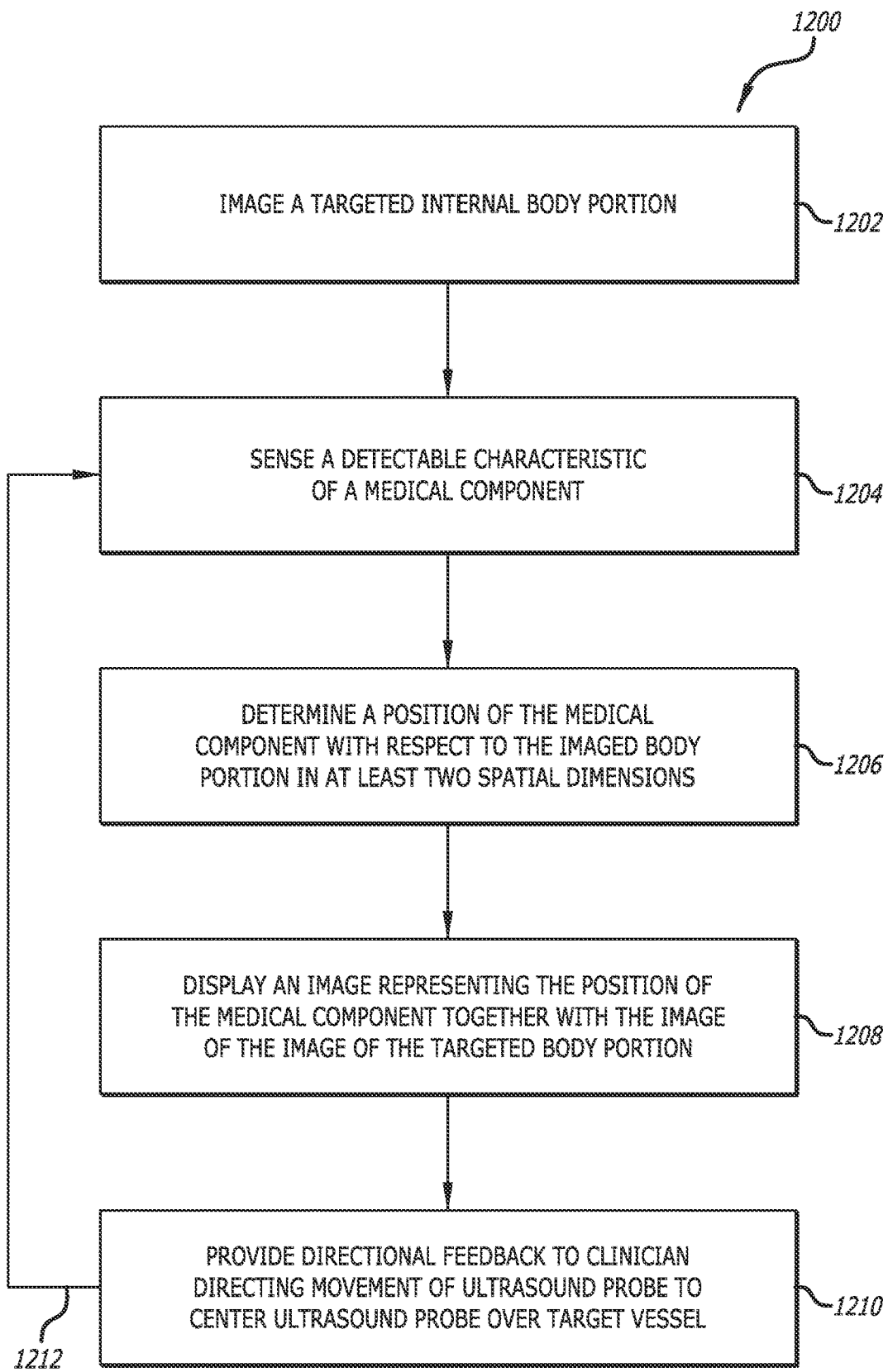
FIG. 12 is a flow diagram illustrating various stages of a method for guiding a needle to a desired target within the body of a patient in accordance with some embodiments.

Referring to FIG. 12, is a flow diagram illustrating various stages of a method for guiding a needle to a desired target within the body of a patient is shown in accordance with some embodiments. Each block illustrated in FIG. 12 represents an operation performed in the method 1200, which begins at stage 1202 where a targeted internal body portion of a patient is imaged by an imaging system, such as an ultrasound imaging device for instance. At stage 1204, a detectable characteristic of a medical component such as a needle is sensed by one or more sensors included with the imaging system. In the present embodiment, the detectable characteristic of the needle is a magnetic field of the magnetic element 1024 included with the needle 1020 and the sensors are magnetic sensors included in the sensor array 1000 included with the ultrasound probe 106.

At stage 1206, a position of the medical component with respect to the targeted internal body portion is determined in at least two spatial dimensions via sensing of the detectable characteristic. As described above, such determination is made in the present embodiment by the processor 116 of the console 1120. At stage 1208, an image representing the position of the medical component is combined with the image of the targeted internal body portion for depiction on a display. At stage 1210, directional feedback is provided to the clinician directing movement (or confirming location) of an ultrasound probe utilized in capturing the image of the internal body portion. The directional feedback may be any as discussed above. Stage 1212 shows that stages 1204-1208 can be iteratively repeated to depict advancement or other movement of the medical component with respect to the imaged target, such as percutaneous insertion of the needle 1020 toward the vessel 1008 (FIGS. 11A, 11B), for instance. It is appreciated that the processor 116 or other suitable component can calculate additional aspects, including the area of image 1039 and the target 1038 (FIGS. 11A, 11B) for depiction on the display 104.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An ultrasound imaging system, comprising:
   an ultrasound probe including an array of ultrasonic transducers and an optical fiber, wherein a portion of the optical fiber extends through at least a portion of the ultrasound probe, wherein the ultrasonic transducers are configured to emit generated ultrasound signals into a patient, receive reflected ultrasound signals from the patient, and convert the reflected ultrasound signals into corresponding electrical signals for processing into ultrasound images, and wherein the optical fiber includes a set of gratings disposed along a length of the optical fiber, and wherein the portion of the optical fiber extending through the portion of the ultrasound probe is configured in a predetermined geometry relative to the ultrasonic transducers; and
   a console configured to communicate with the ultrasound probe, the console including one or more processors and a non-transitory computer-readable medium having stored thereon logic, when executed by the one or more processors, causes operations including:
      obtaining orientation information of the ultrasound probe through analysis of reflected light signals reflected by the set of gratings in view of the predetermined geometry relative to the ultrasonic transducers;
      performing an identification process on the reflected ultrasound signals to identify a target vessel;
      determining, based on the orientation information, a direction of movement resulting in placement of a center of the ultrasound probe over an anatomical target; and
      initiating provision of feedback to a user of the ultrasound probe indicating the direction of movement resulting in the placement of the center of the ultrasound probe over the anatomical target.

2. The ultrasound imaging system of claim 1, wherein the orientation information indicates positioning of the ultrasound probe on a Cartesian coordinate system relative to a skin surface of the patient.

3. The ultrasound imaging system of claim 1, wherein the optical fiber includes one or more core fibers, wherein each of the one or more core fibers includes a plurality of gratings distributed along a longitudinal length of a corresponding core fiber and each sensor of the plurality of gratings is configured to (i) reflect a light signal of a different spectral width based on received incident light, and (ii) change a characteristic of the reflected light signal for use in determining a physical state of the optical fiber.

4. The ultrasound imaging system of claim 3, wherein the operations further include:
   providing a broadband incident light signal to the optical fiber,
   receiving a reflected light signal of the broadband incident light signal, and
   processing the reflected light signal to determine the orientation information.

5. The ultrasound imaging system of claim 1, wherein the identification process includes applying a trained machine learning model configured to detect anatomical features within the ultrasound images and provide a bounding box around the anatomical target.

6. The ultrasound imaging system of claim 1, wherein the provision of the feedback includes providing haptic feedback from a first side of the ultrasound probe, where the first side corresponds to the direction of movement required by the ultrasound probe to place the ultrasound probe at a position relative to the ultrasound probe over the anatomical target.

7. The ultrasound imaging system of claim 1, further comprising:
a needle including a second optical fiber configured to obtain needle orientation information, and wherein the operations further include:
determining, based on the needle orientation information, an orientation of the needle relative to the ultrasound probe,
determining a trajectory of the needle, and
generating a display screen illustrating the trajectory of the needle.

8. A method of performing an ultrasound procedure comprising:
providing an ultrasound probe including an array of ultrasonic transducers and an optical fiber, wherein a portion of the optical fiber extends through at least a portion of the ultrasound probe, wherein the ultrasonic transducers are configured to emit generated ultrasound signals into a patient, receive reflected ultrasound signals from the patient, and convert the reflected ultrasound signals into corresponding electrical signals for processing into ultrasound images, and wherein the optical fiber includes a set of gratings disposed along a length of the optical fiber, and wherein the portion of the_optical fiber extending through the portion of the ultrasound probe is configured in a predetermined geometry relative to the ultrasonic transducers;
providing a console configured to communicate with the ultrasound probe, the console including one or more processors and a non-transitory computer-readable medium having stored thereon logic that, when executed by the one or more processors, causes operations; and
instructing use of the ultrasound probe and the console to cause execution of the one or more processors of the console to perform operations including:
obtaining orientation information of the ultrasound probe through analysis of reflected light signals reflected by the set of gratings in view of the predetermined geometry relative to the ultrasonic transducers;
performing an identification process on the reflected ultrasound signals to identify a target vessel;
determining, based on the orientation information, a direction of movement resulting in placement of a center of the ultrasound probe over an anatomical target; and
initiating provision of feedback to a user of the ultrasound probe indicating the direction of movement resulting in the placement of the center of the ultrasound probe over the anatomical target.

9. The method of claim 8, wherein the orientation information indicates positioning of the ultrasound probe on a Cartesian coordinate system relative to a skin surface of the patient.

10. The method of claim 8, wherein the optical fiber includes one or more core fibers, wherein each of the one or more core fibers includes a plurality of gratings distributed along a longitudinal length of a corresponding core fiber and each sensor of the plurality of gratings is configured to (i) reflect a light signal of a different spectral width based on received incident light, and (ii) change a characteristic of the reflected light signal for use in determining a physical state of the optical fiber.

11. The method of claim 10, wherein the operations further include:
providing a broadband incident light signal to the optical fiber,
receiving a reflected light signal of the broadband incident light signal, and
processing the reflected light signal to determine the orientation information.

12. The method of claim 8, wherein the identification process includes applying a trained machine learning model configured to detect anatomical features within the ultrasound images and provide a bounding box around the anatomical target.

13. The method of claim 8, wherein the provision of the feedback includes providing haptic feedback from a first side of the ultrasound probe, where the first side corresponds to the direction of movement required by the ultrasound probe to place the ultrasound probe at a position relative to the ultrasound probe over the anatomical target.

14. The method of claim 8, further comprising:
providing a needle including a second optical fiber configured to obtain needle orientation information, and wherein the operations further include:
determining, based on the needle orientation information, an orientation of the needle relative to the ultrasound probe,
determining a trajectory of the needle, and
generating a display screen illustrating the trajectory of the needle.

15. A non-transitory, computer-readable medium having stored thereon logic that, when executed by one or more processors, causes performance of operations comprising:
obtaining orientation information of an ultrasound probe, wherein the ultrasound probe includes an array of ultrasonic transducers and an optical fiber, wherein a portion of the optical fiber extends through at least a portion of the ultrasound probe, wherein the ultrasonic transducers are configured to emit generated ultrasound signals into a patient, receive reflected ultrasound signals from the patient, and convert the reflected ultrasound signals into corresponding electrical signals for processing into ultrasound images, and wherein the optical fiber includes a set of gratings disposed along a length of the optical fiber, and wherein the portion of the optical fiber extending through the portion of the ultrasound probe is configured in a predetermined geometry relative to the ultrasonic transducers;
performing an identification process on the reflected ultrasound signals to identify an anatomical target;
determining, based on the orientation information, a direction of movement resulting in placement of a center of the ultrasound probe over the anatomical target; and
initiating provision of feedback to a user of the ultrasound probe indicating the direction of movement resulting in the placement of the center of the ultrasound probe over the anatomical target.

16. The non-transitory, computer-readable medium of claim 15, wherein the optical fiber includes one or more core fibers, wherein each of the one or more core fibers includes a plurality of gratings distributed along a longitudinal length of a corresponding core fiber and each sensor of the plurality of gratings is configured to (i) reflect a light signal of a different spectral width based on received incident light, and (ii) change a characteristic of the reflected light signal for use in determining a physical state of the optical fiber, and wherein the operations further include:

providing a broadband incident light signal to the optical fiber, receiving a reflected light signal of the broadband incident light signal, and processing the reflected light signal to determine the orientation information.

17. The non-transitory, computer-readable medium of claim 16, wherein the provision of the feedback includes providing haptic feedback from a first side of the ultrasound probe, where the first side corresponds to the direction of movement required by the ultrasound probe to place the ultrasound probe at a position relative to the ultrasound probe over the anatomical target.

* * * * *